(12) United States Patent
Miles et al.

(10) Patent No.: US 8,137,284 B2
(45) Date of Patent: Mar. 20, 2012

(54) SURGICAL ACCESS SYSTEM AND RELATED METHODS

(75) Inventors: Patrick Miles, San Diego, CA (US);
Scott Martinelli, Mountain Top, PA (US); Eric Finley, Poway, CA (US); James Gharib, San Diego, CA (US); Allen Farquhar, San Diego, CA (US); Norbert Kaula, Arvada, CO (US); Jeffrey Blewett, San Diego, CA (US); Goretti Medeiros, legal representative, Plantsville, CT (US)

(73) Assignee: NuVasive, Inc., San Diego, CA (US)

( * ) Notice: Subject to any disclaimer, the term of this patent is extended or adjusted under 35 U.S.C. 154(b) by 936 days.

(21) Appl. No.: 10/682,568

(22) Filed: Oct. 8, 2003

(65) Prior Publication Data
US 2008/0058606 A1 Mar. 6, 2008

Related U.S. Application Data

(60) Provisional application No. 60/417,235, filed on Oct. 8, 2002.

(51) Int. Cl.
*A61B 5/05* (2006.01)
(52) U.S. Cl. .......................... 600/554; 606/32
(58) Field of Classification Search .................. 600/201, 600/211, 214, 546, 554, 184, 227, 231, 232, 600/202; 606/86, 90, 105, 32, 41, 108
See application file for complete search history.

(56) References Cited

U.S. PATENT DOCUMENTS

| 208,227 | A | 9/1878 | Dorr |
| 972,983 | A | 10/1910 | Arthur |
| 1,328,624 | A | 1/1920 | Graham |
| 1,548,184 | A | 8/1925 | Cameron |
| 2,704,064 | A | 3/1955 | Fizzell et al. ................ 128/2.1 |
| 2,736,002 | A | 2/1956 | Oriel |
| 2,808,826 | A | 10/1957 | Reiner et al. |
| 3,364,929 | A | 1/1968 | Ide et al. .................... 128/172.1 |
| 3,664,329 | A | 5/1972 | Naylor ....................... 128/2.1 R |

(Continued)

FOREIGN PATENT DOCUMENTS

DE 299 08 259 7/1999

(Continued)

OTHER PUBLICATIONS

"Electromyography System", *International Search Report*, International Application No. PCT/US00/32329,(Apr. 27, 2001), 9 pages.

(Continued)

*Primary Examiner* — Victor Nguyen
(74) *Attorney, Agent, or Firm* — Jonathan Spangler; Rory Schermerhorn; Fish & Richardson P.C.

(57) ABSTRACT

A system for accessing a surgical target site and related methods, involving an initial distraction system for creating an initial distraction corridor, and an assembly capable of distracting from the initial distraction corridor to a secondary distraction corridor and thereafter sequentially receiving a plurality of retractor blades for retracting from the secondary distraction corridor to thereby create an operative corridor to the surgical target site, both of which may be equipped with one or more electrodes for use in detecting the existence of (and optionally the distance and/or direction to) neural structures before, during, and after the establishment of an operative corridor to a surgical target site.

48 Claims, 17 Drawing Sheets

U.S. PATENT DOCUMENTS

| | | | |
|---|---|---|---|
| 3,682,162 A | 8/1972 | Colyer | 128/2.1 R |
| 3,785,368 A | 1/1974 | McCarthy et al. | 128/2.1 Z |
| 3,830,226 A | 8/1974 | Staub et al. | 128/2.1 R |
| 3,957,036 A | 5/1976 | Normann | 128/2.1 R |
| 4,099,519 A | 7/1978 | Warren | 128/2.1 R |
| 4,164,214 A | 8/1979 | Stark et al. | |
| 4,207,897 A | 6/1980 | Lloyd et al. | 128/303.1 |
| 4,224,949 A | 9/1980 | Scott et al. | 128/734 |
| 4,226,228 A | 10/1980 | Shin et al. | |
| 4,235,242 A | 11/1980 | Howson et al. | 128/695 |
| 4,285,347 A | 8/1981 | Hess | 128/785 |
| 4,291,705 A | 9/1981 | Severinghaus et al. | 600/546 |
| 4,461,300 A | 7/1984 | Christensen | |
| 4,515,168 A | 5/1985 | Chester et al. | 128/741 |
| 4,519,403 A | 5/1985 | Dickhudt | 128/785 |
| 4,545,374 A | 10/1985 | Jacobson | |
| 4,561,445 A | 12/1985 | Berke et al. | 128/642 |
| 4,562,832 A | 1/1986 | Wilder et al. | |
| 4,573,448 A | 3/1986 | Kambin | |
| 4,592,369 A | 6/1986 | Davis et al. | 128/733 |
| 4,595,018 A | 6/1986 | Rantala | 128/733 |
| 4,611,597 A | 9/1986 | Kraus | |
| 4,633,889 A | 1/1987 | Talalla et al. | 128/784 |
| 4,658,835 A | 4/1987 | Pohndorf | 128/785 |
| 4,744,371 A | 5/1988 | Harris | 607/117 |
| 4,759,377 A | 7/1988 | Dykstra | 128/733 |
| 4,784,150 A | 11/1988 | Voorhies et al. | |
| 4,807,642 A | 2/1989 | Brown | 128/733 |
| 4,892,105 A | 1/1990 | Prass | 128/741 |
| 4,913,134 A | 4/1990 | Luque | |
| 4,926,865 A | 5/1990 | Oman | 128/421 |
| 4,962,766 A | 10/1990 | Herzon | 128/741 |
| 4,964,411 A | 10/1990 | Johnson et al. | 128/733 |
| 5,007,902 A | 4/1991 | Witt | 604/117 |
| 5,058,602 A | 10/1991 | Brody | 128/733 |
| 5,081,990 A | 1/1992 | Deletis | 128/642 |
| 5,092,344 A | 3/1992 | Lee | 128/741 |
| 5,127,403 A | 7/1992 | Brownlee | 128/419 P |
| 5,161,533 A | 11/1992 | Prass et al. | 128/639 |
| 5,171,279 A | 12/1992 | Mathews | |
| 5,195,541 A | 3/1993 | Obenchain | |
| 5,196,015 A | 3/1993 | Neubardt | 606/61 |
| RE34,390 E | 9/1993 | Culver | 128/731 |
| 5,255,691 A | 10/1993 | Otten | 607/117 |
| 5,282,468 A | 2/1994 | Klepinski | 128/642 |
| 5,284,153 A | 2/1994 | Raymond et al. | 128/741 |
| 5,284,154 A | 2/1994 | Raymond et al. | 128/741 |
| 5,295,994 A | 3/1994 | Bonutti | |
| 5,299,563 A | 4/1994 | Seton | |
| 5,312,417 A | 5/1994 | Wilk | 606/114 |
| 5,313,956 A | 5/1994 | Knutsson et al. | 128/741 |
| 5,313,962 A | 5/1994 | Obenchain | |
| 5,327,902 A | 7/1994 | Lemmen | 128/734 |
| 5,331,975 A | 7/1994 | Bonutti | |
| 5,333,618 A | 8/1994 | Lekhtman et al. | 128/734 |
| 5,342,384 A | 8/1994 | Sugarbaker | |
| 5,375,067 A | 12/1994 | Berchin | 364/487 |
| 5,383,876 A | 1/1995 | Nardella | 606/49 |
| 5,395,317 A | 3/1995 | Kambin | |
| 5,450,845 A | 9/1995 | Axelgaard | |
| 5,474,057 A | 12/1995 | Makower et al. | |
| 5,474,558 A | 12/1995 | Neubardt | 606/79 |
| 5,480,440 A | 1/1996 | Kambin | |
| 5,482,038 A | 1/1996 | Ruff | 128/642 |
| 5,484,437 A | 1/1996 | Michelson | |
| 5,509,893 A | 4/1996 | Pracas | |
| 5,514,153 A | 5/1996 | Bonutti | |
| 5,540,235 A | 7/1996 | Wilson | 128/741 |
| 5,549,656 A | 8/1996 | Reiss | 607/48 |
| 5,560,372 A | 10/1996 | Cory | 128/741 |
| 5,566,678 A | 10/1996 | Cadwell | 128/731 |
| 5,571,149 A | 11/1996 | Liss et al. | |
| 5,579,781 A | 12/1996 | Cooke | 128/733 |
| 5,593,429 A | 1/1997 | Ruff | 607/116 |
| 5,599,279 A * | 2/1997 | Slotman et al. | 600/201 |
| 5,630,813 A | 5/1997 | Kieturakis | 606/46 |
| 5,667,508 A | 9/1997 | Errico et al. | |
| 5,671,752 A | 9/1997 | Sinderby et al. | 128/733 |
| 5,681,265 A | 10/1997 | Maeda et al. | |
| 5,707,359 A | 1/1998 | Bufalini | 604/104 |
| 5,711,307 A | 1/1998 | Smits | 128/733 |
| 5,728,046 A * | 3/1998 | Mayer et al. | 600/210 |
| 5,741,253 A | 4/1998 | Michelson | |
| 5,759,159 A | 6/1998 | Masreliez | |
| 5,762,629 A | 6/1998 | Kambin | |
| 5,772,661 A | 6/1998 | Michelson | |
| 5,775,331 A | 7/1998 | Raymond et al. | 128/741 |
| 5,776,144 A | 7/1998 | Leysieffer et al. | |
| 5,779,642 A | 7/1998 | Nightengale | 600/461 |
| 5,785,658 A | 7/1998 | Benaron et al. | |
| 5,792,044 A | 8/1998 | Foley et al. | |
| 5,797,854 A | 8/1998 | Hedgecock | 600/554 |
| 5,814,073 A | 9/1998 | Bonutti | 606/232 |
| 5,830,151 A | 11/1998 | Hadzic et al. | 600/554 |
| 5,851,191 A | 12/1998 | Gozani | 600/554 |
| 5,853,373 A | 12/1998 | Griffith et al. | 600/554 |
| 5,860,973 A | 1/1999 | Michelson | |
| 5,862,314 A | 1/1999 | Jeddeloh | |
| 5,872,314 A | 2/1999 | Clinton | |
| 5,885,210 A | 3/1999 | Cox | |
| 5,885,219 A | 3/1999 | Nightengale | 600/461 |
| 5,888,196 A | 3/1999 | Bonutti | 600/204 |
| 5,891,147 A | 4/1999 | Moskovitz et al. | |
| 5,902,231 A | 5/1999 | Foley et al. | |
| 5,928,139 A | 7/1999 | Koros | |
| 5,928,158 A | 7/1999 | Aristides | 600/547 |
| 5,935,131 A | 8/1999 | Bonutti et al. | |
| 5,938,688 A | 8/1999 | Schiff | |
| 5,944,658 A | 8/1999 | Koros et al. | |
| 5,976,094 A | 11/1999 | Gozani et al. | 600/483 |
| 6,004,262 A | 12/1999 | Putz et al. | 600/114 |
| 6,004,312 A | 12/1999 | Finneran | |
| 6,007,487 A | 12/1999 | Foley et al. | |
| 6,024,696 A | 2/2000 | Hoftman et al. | |
| 6,027,456 A | 2/2000 | Feler et al. | 600/554 |
| 6,038,469 A | 3/2000 | Karlsson et al. | |
| 6,038,477 A | 3/2000 | Kayyali | 607/72 |
| 6,050,992 A | 4/2000 | Nichols | 606/41 |
| 6,074,343 A | 6/2000 | Nathanson et al. | |
| 6,095,987 A | 8/2000 | Shmulewitz et al. | |
| 6,104,957 A | 8/2000 | Alo et al. | 607/46 |
| 6,104,960 A | 8/2000 | Duysens et al. | |
| 6,120,503 A | 9/2000 | Michelson | |
| 6,126,660 A | 10/2000 | Dietz | |
| 6,132,386 A | 10/2000 | Gozani et al. | 600/554 |
| 6,132,387 A | 10/2000 | Gozani et al. | 600/554 |
| 6,135,965 A | 10/2000 | Tumer et al. | 600/476 |
| 6,139,493 A | 10/2000 | Koros et al. | |
| 6,146,335 A | 11/2000 | Gozani | 600/554 |
| 6,152,871 A | 11/2000 | Foley et al. | |
| 6,161,047 A | 12/2000 | King et al. | 607/62 |
| 6,174,311 B1 | 1/2001 | Branch et al. | |
| 6,181,961 B1 | 1/2001 | Prass | |
| 6,196,969 B1 | 3/2001 | Bester et al. | |
| 6,206,826 B1 * | 3/2001 | Mathews et al. | 600/210 |
| 6,217,509 B1 | 4/2001 | Foley et al. | |
| 6,224,549 B1 | 5/2001 | Drongelen | 600/300 |
| 6,259,945 B1 | 7/2001 | Epstein et al. | 600/547 |
| 6,264,651 B1 | 7/2001 | Underwood et al. | |
| 6,266,558 B1 | 7/2001 | Gozani et al. | 600/547 |
| 6,273,905 B1 | 8/2001 | Streeter | |
| 6,292,701 B1 | 9/2001 | Prass et al. | 607/116 |
| 6,306,100 B1 | 10/2001 | Prass | |
| 6,308,712 B1 | 10/2001 | Shaw | |
| 6,312,392 B1 | 11/2001 | Herzon | 600/554 |
| 6,325,764 B1 | 12/2001 | Griffith et al. | |
| 6,334,068 B1 | 12/2001 | Hacker | |
| 6,348,058 B1 | 2/2002 | Melkent et al. | |
| 6,360,750 B1 | 3/2002 | Gerber et al. | |
| 6,425,859 B1 | 7/2002 | Foley et al. | |
| 6,425,901 B1 * | 7/2002 | Zhu et al. | 606/142 |
| 6,450,952 B1 | 9/2002 | Rioux et al. | |
| 6,451,015 B1 | 9/2002 | Rittman, III et al. | |
| 6,466,817 B1 | 10/2002 | Kaula et al. | 600/546 |
| 6,468,205 B1 | 10/2002 | Mollenauer et al. | |
| 6,468,207 B1 | 10/2002 | Fowler, Jr. | |
| 6,500,128 B2 | 12/2002 | Marino | 600/554 |

| | | | |
|---|---|---|---|
| 6,520,907 B1 | 2/2003 | Foley et al. | |
| 6,524,320 B2 | 2/2003 | DiPoto | |
| 6,535,759 B1 | 3/2003 | Epstein et al. | |
| 6,564,078 B1 | 5/2003 | Marino et al. | 600/373 |
| 6,579,244 B2 | 6/2003 | Goodwin | |
| 6,620,157 B1 | 9/2003 | Dabney et al. | |
| 6,645,194 B2 | 11/2003 | Briscoe et al. | |
| 6,679,833 B2 | 1/2004 | Smith et al. | |
| 6,719,692 B2 | 4/2004 | Kleffner et al. | |
| 6,760,616 B2 | 7/2004 | Hoey et al. | |
| 6,770,074 B2 | 8/2004 | Michelson | |
| 6,796,985 B2 | 9/2004 | Bolger et al. | |
| 6,810,281 B2 | 10/2004 | Brock et al. | |
| 6,819,956 B2 | 11/2004 | DiLorenzo | |
| 6,847,849 B2 | 1/2005 | Mamo et al. | |
| 6,849,047 B2 | 2/2005 | Goodwin | |
| 6,855,105 B2 | 2/2005 | Jackson, III et al. | |
| 6,902,569 B2 | 6/2005 | Parmer et al. | |
| 6,926,728 B2 | 8/2005 | Zucherman et al. | |
| 6,929,606 B2 * | 8/2005 | Ritland | 600/201 |
| 6,945,933 B2 | 9/2005 | Branch | |
| 6,951,538 B2 | 10/2005 | Ritland | |
| 7,047,082 B1 | 5/2006 | Schrom et al. | |
| 7,050,848 B2 | 5/2006 | Hoey et al. | |
| 7,079,883 B2 | 7/2006 | Marino et al. | |
| 7,089,059 B1 | 8/2006 | Pless | |
| 7,177,677 B2 | 2/2007 | Kaula et al. | |
| 7,198,598 B2 | 4/2007 | Smith et al. | |
| 7,207,949 B2 * | 4/2007 | Miles et al. | 600/554 |
| 7,226,451 B2 | 6/2007 | Shluzas et al. | |
| 7,261,688 B2 | 8/2007 | Smith et al. | |
| 7,470,236 B1 | 12/2008 | Kelleher et al. | |
| 7,473,222 B2 | 1/2009 | Dewey et al. | |
| 7,481,766 B2 | 1/2009 | Lee et al. | |
| 7,582,058 B1 | 9/2009 | Miles et al. | |
| 7,643,884 B2 | 1/2010 | Pond et al. | |
| 7,691,057 B2 | 4/2010 | Miles et al. | |
| 7,819,801 B2 | 10/2010 | Miles et al. | |
| 2001/0039949 A1 | 11/2001 | Loubser | |
| 2001/0056280 A1 | 12/2001 | Underwood et al. | |
| 2002/0007129 A1 | 1/2002 | Marino | 600/546 |
| 2002/0010392 A1 | 1/2002 | Desai | |
| 2002/0072686 A1 | 6/2002 | Hoey et al. | 600/547 |
| 2002/0123780 A1 | 9/2002 | Grill et al. | |
| 2002/0161415 A1 | 10/2002 | Cohen et al. | |
| 2002/0193843 A1 | 12/2002 | Hill et al. | |
| 2003/0032966 A1 | 2/2003 | Foley et al. | |
| 2003/0105503 A1 | 6/2003 | Marino | |
| 2003/0139648 A1 | 7/2003 | Foley et al. | |
| 2003/0149341 A1 | 8/2003 | Clifton | |
| 2003/0225405 A1 | 12/2003 | Weiner | |
| 2003/0236544 A1 | 12/2003 | Lunsford et al. | |
| 2004/0199084 A1 | 10/2004 | Kelleher et al. | |
| 2004/0225228 A1 | 11/2004 | Ferree | |
| 2005/0004593 A1 * | 1/2005 | Simonson | 606/191 |
| 2005/0004623 A1 | 1/2005 | Miles et al. | |
| 2005/0033380 A1 | 2/2005 | Tanner et al. | |
| 2005/0075578 A1 * | 4/2005 | Gharib et al. | 600/546 |
| 2005/0080320 A1 | 4/2005 | Lee et al. | |
| 2005/0149035 A1 | 7/2005 | Pimenta et al. | |
| 2005/0182454 A1 | 8/2005 | Gharib et al. | |
| 2005/0192575 A1 | 9/2005 | Pacheco | |
| 2006/0025703 A1 | 2/2006 | Miles et al. | |
| 2006/0052828 A1 | 3/2006 | Kim et al. | |
| 2006/0069315 A1 | 3/2006 | Miles et al. | |
| 2006/0224078 A1 | 10/2006 | Hoey et al. | |
| 2007/0016097 A1 | 1/2007 | Farquhar et al. | |
| 2007/0198062 A1 | 8/2007 | Miles et al. | |
| 2007/0293782 A1 | 12/2007 | Marino | |
| 2008/0058606 A1 | 3/2008 | Miles et al. | |
| 2008/0064976 A1 | 3/2008 | Kelleher et al. | |
| 2008/0064977 A1 | 3/2008 | Kelleher et al. | |
| 2008/0065178 A1 | 3/2008 | Kelleher et al. | |
| 2008/0071191 A1 | 3/2008 | Kelleher et al. | |
| 2008/0097164 A1 | 4/2008 | Miles et al. | |
| 2008/0300465 A1 | 12/2008 | Feigenwinter et al. | |
| 2009/0124860 A1 | 5/2009 | Miles et al. | |
| 2009/0138050 A1 | 5/2009 | Ferree | |
| 2009/0192403 A1 | 7/2009 | Gharib et al. | |
| 2009/0204016 A1 | 8/2009 | Gharib et al. | |
| 2010/0069783 A1 | 3/2010 | Miles et al. | |
| 2010/0130827 A1 | 5/2010 | Pimenta et al. | |
| 2010/0152603 A1 | 6/2010 | Miles et al. | |
| 2010/0160738 A1 | 6/2010 | Miles et al. | |
| 2010/0174148 A1 | 7/2010 | Miles et al. | |

FOREIGN PATENT DOCUMENTS

| | | |
|---|---|---|
| EP | 0 972 538 | 1/2000 |
| FR | 2 795 624 | 1/2001 |
| WO | WO 00/38574 | 7/2000 |
| WO | WO 00/67645 | 11/2000 |
| WO | WO-0066217 A1 | 11/2000 |
| WO | WO 01/37728 | 5/2001 |
| WO | WO 02/054960 | 7/2002 |
| WO | WO 2003/005887 | 1/2003 |
| WO | WO-03026482 A2 | 4/2003 |
| WO | WO-03037170 A2 | 5/2003 |
| WO | WO-03037170 A3 | 5/2003 |
| WO | WO-2005013805 A3 | 2/2005 |
| WO | WO 2005/030318 | 4/2005 |
| WO | WO-2006042241 A2 | 4/2006 |
| WO | WO 2006/066217 | 6/2006 |

OTHER PUBLICATIONS

"Nerve Proximity and Status Detection System and Method", *International Search Report*, International Application No. PCT/US01/18606,(Oct. 18, 2001), 6 pages.

"Relative Nerve Movement and Status Detection System and Method", *International Search Report*, International Application No. PCT/US01/18579,(Jan. 15, 2002), 6 pages.

"System and Method for Determining Nerve Proximity, Direction, and Pathology During Surgery", International Search Report, International Application No. PCT/US02/22247,(Mar. 27, 2003), 4 pages.

"System and Methods for Determining Nerve Direction a Surgical Instrument", *International Search Report*, International Application to No. PCT/US03/02056,(Aug. 12, 2003), 5 pages.

"Systems and Methods for Performing Percutaneous Pedicle Integrity Assessments", *International Search Report*, International Application No. PCT/US02/35047,(Aug. 11, 2003), 5 pages.

"Systems and Methods for Performing Surgery Procedures and Assessments", *International Search Report*, International Application No. PCT/US02/30617,(Jun. 5, 2003), 4 pages.

Bose, et al., "Neurophysiologic Monitoring of Spinal Nerve Root Function During Instrumented Posterior Lumbar Spine Surgery", *Spine*, 27(13), (2002), pp. 1444-1450.

Calancie, et al., "Stimulus-Evoked EMG Monitoring During Transpedicular Lumbosacral Spine Instrumentation", *Spine*, 19(24), (1994), pp. 2780-2786.

Clements, et al., "Evoked and Spontaneous Electromyography to Evaluate Lumbosacral Pedicle Screw Placement", *Spine*, 21(5), (1996),pp. 600-604.

Ford, et al., "Electrical Characteristics of Peripheral Nerve Stimulators Implications for Nerve Localization", *Regional Anesthesia*, 9 (1984), pp. 73-77.

Glassman, et al., "A Prospective Analysis of Intraoperative Electromyographic Monitoring of Pedicle Screw Placement With Computed Tomographic Scan Confirmation", *Spine*, 20(12), (1995), pp. 1375-1379.

Greenblatt, et al., "Needle Nerve Stimulator-Locator: Nerve Blocks with a New Instrument for Locating Nerves", *Anesthesia & Analgesia*, 41(5), (1962), pp. 599-602.

Holland, N. , "Intraoperative Electromyography During Thoracolumbar Spinal Surgery", *Spine*, 23(17), (1998), pp. 1915-1922.

Lenke, et al., "Triggered Electromyographic Threshold for Accuracy of Pedicle Screw Placement", *Spine*, 20(14), (1995),1585-1591.

Maguire, et al., "Evaluation of Intrapedicular Screw Position Using Intraoperative Evoked Electromyography", *Spine*, 20(9), (1995), pp. 1068-1074.

Martin, et al., "Initiation of Erection and Semen Release by Rectal Probe Electrostimulation (RPE)", *The Williams & Wilkins Co.*, (1983), pp. 637-642.

Pither, et al., "'The Use of Peripheral Nerve Stimulators for Regional Anesthesia: Review of Experimental Characteristics, Technique, and Clinical Applications'", *Regional Anesthesia*, (1985), pp. 10:47-53.
Raj, et al., "Infraclavicular Brachial Plexus Block—A New Approach", *Anesthesia and Analgesia*, (1973), pp. 897-904.
Raj, et al., "The Use of Peripheral Nerve Stimulators for Regional Anesthesia", *Clinical Issues in Regional Anesthesia*, 1 (4), (1985), pp. 1-6.
Raj, et al., "Use of the nerve Stimulator of Peripheral Blocks", Regional Anesthesia, (Apr.-Jun. 1980), pp. 14-21.
Raymond, et al., "The Nerve Seeker: A System for Automated Nerve Localization", *Regional Anesthesia*, 17(3), (1992), pp. 151-162.
Shafik, "Cavernous Nerve Simulation through an Extrapelvic Subpubic Approach: Role in Pencil Erection", *Eur. Urol*, 26, (1994), pp. 98-102.
Toleikis, et al., "The Usefulness of Electrical Stimulation for Assessing Pedicle Screw Replacements", *Journal of Spinal Disorder*, 13(4), (2000), pp. 283-289.
"Brackmann II EMG System", *Medical Electronics*, (1999), 4 pages.
"Neurovision SE Nerve Locator/Monitor", *RLN Systems. Inc. Operators Manual*, (1999), 22 pages.
"The Brackmann II EMG Monitoring System", *Medical Electronics Co. Operator's Manual Version 1.1*, (1995), 50 pages.
"The Nicolet Viking IV", *Nicolet Biomedical Products*, (1999), 6 pages.
Anderson, D. G., et al., "Pedicle screws with high electrical resistance: a potential source of error with stimulus-evoked EMG", *Spine*. 27(14):, Department of Orthopaedic Surgery, University of Virginia,(Jul. 15, 2002),1577-1581.
Danesh-Clough, T., "The use of evoked EMG in detecting misplaced thoracolumbar pedicle screws", *Spine*. 26(12), Orthopaedic Department, Dunedin Hospital, (Jun. 15, 2001), 1313-1316.
Darden, B. V., et al., "A comparison of impedance and electromyogram measurements in detecting the presence of pedicle wall breakthrough", *Spine*. 23(2), Charlotte Spine Center, North Carolina, (Jan. 15, 1998), 256-262.
Ebraheim, N. A., et al., "Anatomic relations between the lumbar pedicle and the adjacent neural structures", *Spine*. 22(20), Department of Orthopaedic Surgery, Medical College of Ohio, (Oct. 15, 1997), 2338-2341.
Haig, "Point of view", *Spine* 27 (24), 2819.
Haig, A. J., et al., "The relation among spinal geometry on MRI, paraspinal electromyographic abnormalities, and age in persons referred for electrodiagnostic testing of low back symptoms", *Spine*. 27(17), Department of Physical Medicine and Rehabilitation, University of Michigan, (Sep. 1, 2002), 1918-1925.
Holland, N. R., et al., "Higher electrical stimulus intensities are required to activate chronically compressed nerve roots. Implications for intraoperative electromyographic pedicle screw testing", *Spine*. 23(2), Department of Neurology, Johns Hopkins University School of Medicine, (Jan. 15, 1998), 224-227.
Minahan, R. E., et al., "The effect of neuromuscular blockage on pedicle screw stimulation thresholds", *Spine*. 25(19), Department of Neurology, John Hopkins University, School of Medicine, (Oct. 1, 2000), 2526-2530.
Anatomy of the Lumbar Spine in MED TM MicroEndoscopic Discectomy (1997 Ludann Grand Rapids MI), 14 pgs.
Dirksmeier et al., "Microendoscopic and Open Laminotomy and Discectomy in Lumbar Disc Disease" *Seminars in Spine Surgery*, 1999, 11(2): 138-146.
METRx Delivered Order Form, 1999, 13 pages.
Medtronic Sofamor Danek "METRx™ MicroDisectomy System," *Medtronic Sofamor Danek USA*, 2000, 21 pgs.
Medtronic Sofamor Danek "METRx System Surgical Technique," 2004, 22 pages.
"MetRx System MicroEndoscopic Discectomy: An Evolution in Minimally Invasive Spine Surgery," *Sofamor Danek*, 1999, 6 pages.
Smith and Foley "MetRx System MicroEndoscopic Discectomy: Surgical Technique" *Medtronic Sofamor Danek*, 2000, 24 pages.
"Sofamor Danek MED Microendoscopic Discectomy System Brochure" including Rapp "New endoscopic lumbar technique improves access preserves tissue" Reprinted with permission from: *Orthopedics Today*, 1998, 18(1): 2 pages.

Japanese Patent Office JP Patent Application No. 2006-528306 Office Action with English Translation, Jun. 10, 2009, 4 pages.
Plaintiffs' Preliminary Invalidity Contentions re US Patents 7207949; 7470236 and 7582058, Sep. 18, 2009, 19 pages.
Plaintiffs' Preliminary Invalidity Contentions-Appendices, Sep. 18, 2009, 191 pages.
Plaintiffs' Supplemental Preliminary Invalidity Contentions re US Patents 7207949, 7470236, and 7582058, Sep. 29, 2009, 21 pages.
Plaintiffs' Supplemental Preliminary Invalidity Contentions-Appendices, Sep. 29, 2009, 294 pages.
Axon 501(k) Notification: Epoch 2000 Neurological Workstation, Dec. 3, 1997, 464 pages.
Foley and Smith, "Microendoscopic Discectomy," *Techniques in Neurosurgery*, 1997, 3(4):301-307.
Medtronic Sofamor Danek "Union™/ Union-L™ Anterior & Lateral Impacted Fusion Devices: Clear choice of stabilization," *Medtronic Sofamor Danek*, 2000, 4 pages.
NuVasive Vector™ Cannulae, 1 page (prior to Sep. 25, 2003).
NuVasive Triad™ Tri-Columnar Spinal EndoArthrodesis™ via Minimally Invasive Guidance, 1 page (prior to Sep. 25, 2003).
NuVasive Triad™ Cortical Bone Allograft, 1 page (prior to Sep. 25, 2003).
NuVasive Vertebral Body Access System, 1 page (prior to Sep. 25, 2003).
Marina, "New Technology for Guided Navigation with Real Time Nerve Surveillance for Minimally Invasive Spine Discectomy & Arthrodesis," *Spineline*, 2000, p. 39.
NuVasive "INS-1 Screw Test," 2001, 10 pages.
NuVasive letter re 510k Neuro Vision JJB System, Oct. 16, 2001, 5 pages.
NuVasive letter re 510k Guided Arthroscopy System, Oct. 5, 1999, 6 pages.
NuVasive letter re 510k INS-1 Intraoperative Nerve Surveillance System, Nov. 13, 2000, 7 pages.
"NuVasive™ Receives Clearance to Market Two Key Elem Minimally Invasive Spine Surgery System," Nov. 27, 2001, 20 pages.
Schick et al., "Microendoscopic lumbar discectomy versus open surgery: an intraoperative EMG study," *Eur Spine J*, 2002, 11: 20-26.
NuVasive letter re: 510(k) for Neurovision JJB System (Summary), Sep. 25, 2001, 28 pages.
NuVasive letter re: Special 510(k) Premarket Notification: Neurovision JJB System (Device Description), Jul. 3, 2003, 18 pages.
NuVasive letter re: Special 510(k) Premarket Notification: Neurovision JJB System (Device Description), Mar. 1, 2004, 16 pages.
NuVasive letter re: Special 510(k) Premarket Notification: Neurovision JJB System (Device Description), May 26, 2005, 17 pages.
NuVasive letter re: 510(k) Premarket Notification: Neurovision JJB System (Device Description), Jun. 24, 2005, 16 pages.
NuVasive letter re: Special 510(k) Premarket Notification: Neurovision JJB System (Device Description), Sep. 14, 2006, 17 pages.
NuVasive 510(k) Premarket Notification: Neurovision JJB System (Device Description), Aug. 20, 2007, 8 pages.
NuVasive letter re: 510(k) Premarket Notification: Guided Spinal Arthroscopy System (Device Description), Feb. 1, 1999, 40 pages.
NuVasive 510(k) Premarket Notification: Spinal System (Summary), Apr. 12, 2004, 10 pages.
NuVasive 510(k) Summary NIM Monitor, Sep. 4, 1998, 4 pages.
NuVasive correspondence re 510(k) Premarket Notification INS-1 Intraoperative Nerve Surveillance System: Section IV Device Description, pp. 12-51 (prior to Sep. 25, 2003).
NuVasive letter re 510(k) Premarket Notification INS-1 Intraoperative Nerve Surveillance System, Aug. 24, 2000, 81 pages.
Isley et al., "Recent Advances in Intraoperative Neuromonitoring of Spinal Cord Function: Pedicle Screw Stimulation Techniques," *American Journal of Electroneurodagnostic Technology*, Jun. 1997, 37(2): 93-126.
Mathews et al., "Laparoscopic Discectomy with Anterior Lumbar Interbody Fusion," *Spine*, 1995, 20(16): 1797-1802.
Rose et al., "Persistently Electrified Pedicle Stimulation Instruments in Spinal Instrumentation: Techniques and Protocol Development," *Spine*, 1997, 22(3): 334-343.
Journee et al., "System for Intra-Operative Monitoring of the Cortical Integrity of the Pedicle During Pedicle Screw Placement in Low- Back Surgery: Design and Clinical Results," *Sensory and Neuromuscular Diagnostic Instrumentation and Data Analysis I, 18th Annual International Conference on Engineering in Medicine and Biology Society*, Amsterdam, 1996, pp. 144-145..

Medtronic Sofamor Danek "Union™/Union-L™ Anterior & Lateral Impacted Fusion Devices: Surgical Technique" *Medtronic Sofamor Danek*, 2001, 20 pages.

Defendant's Disclosure of Asserted Claims and Preliminary Infringement Contentions Regarding USP 7207949; 7470236 and 7582058, Aug. 31, 2009, 21 pages.

Bergey et al., "Endoscopic Lateral Transpsoas Approach to the Lumbar Spine," *Spine*, 2004, 29(15):1681-1688.

Dezawa et al., "Retroperitoneal Laparoscopic Lateral Approach to the Lumbar Spine: A New Approach, Technique, and Clinical Trial," *Journal of Spinal Disorders*, 2000, 13(2): 138-143.

Gardocki, "Tubular diskectomy minimizes collateral damage: A logical progression moves spine surgery forward," *AAOS Now*, 2009, 5 pages.

Hovorka et al., "Five years' experience of retroperitoneal lumbar and thoracolumbar surgery," *Eur Spine J.*, 2000, 9(1): S30-S34.

Kossman et al., "The use of a retractor system (SynFrame) for open, minimal invasive reconstruction of the anterior column of the thoracic and lumbar spine," *Eur Spine J.*, 2001, 10. 396-402.

Mayer, "A New Microsurgical Technique for Minimally Invasive Anterior Lumbar Interbody Fusion," *Spine*, 1997, 22(6): 691-699.

Mayer, "The ALIF Concept," *Eur Spine J.*, 2000, 9(1): S35-S43.

Mayer and Wiechert, "Microsurgical Anterior Approaches to the Lumbar Spine for Interbody Fusion and Total Disc Replacement," *Neurosurgery*, 2002, 51(2): 159-165.

McAfee et al., "Minimally Invasive Anterior Retroperitoneal Approach to the Lumbar Spine: Emphasis on the Lateral BAK," *Spine*, 1998, 23(13): 1476-1484.

Rao, et al. "Dynamic retraction of the psoas muscle to expose the lumbar spine using the retroperitoneal approach," *J. Neurosurg Spine*, 2006, 5: 468-470.

Wolfla et al., "Retroperitoneal lateral lumbar interbody fusion with titanium threaded fusion cages," *J. Neurosurg* (Spine 1), 2002, 96: 50-55.

Crock, H.V. MD., "Anterior Lumbar Interbody Fusion," *Clinical Orthopaedics and Related Research*, No. One Hundred Sixty Five, 1982, pp. 157-163, 13 pages.

Larson and Maiman, "Surgery of the Lumbar Spine," Thieme Medical Publishers, Inc., 1999, pp. 305-319.

Medtronic XOMED Surgical Products, Inc., NIM-Response Nerve Integrity Monitor Intraoperative EMG Monitor User's Guide, Revision B, 2000, 47 pages.

"NuVasive's spine surgery system cleared in the US," Pharm & Medical Industry Week, Dec. 10, 2001, 1 page.

Pimenta, "Initial Clinical Results of Direct Lateral, Minimally Invasive Access to the Lumbar Spine for Disc Nucleus Replacement Using a Novel Neurophysiological Monitoring System." *The 9th IMAST*, May 2002, 1 page.

Pimenta et al., "The Lateral Endoscopic Transpsoas Retroperitoneal Approach (Letra) for Implants in the Lumbar Spine," *World Spine II—Second Interdisciplinary Congress on Spine Care*, Aug. 2003, 2 pages.

\* cited by examiner

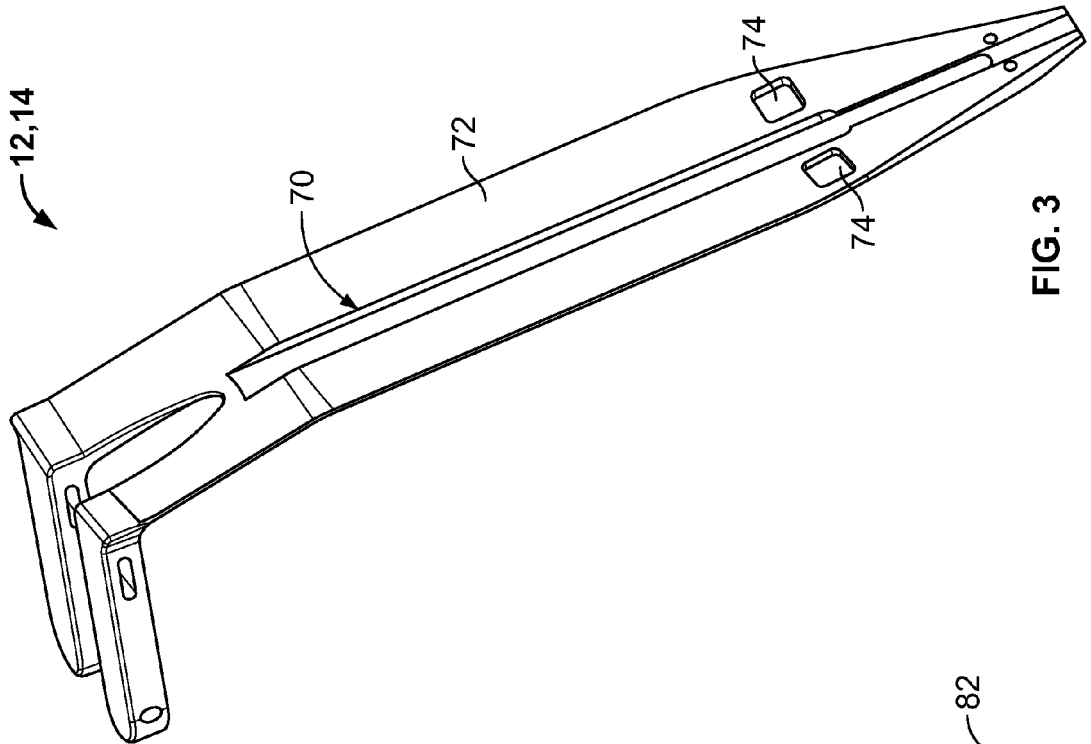
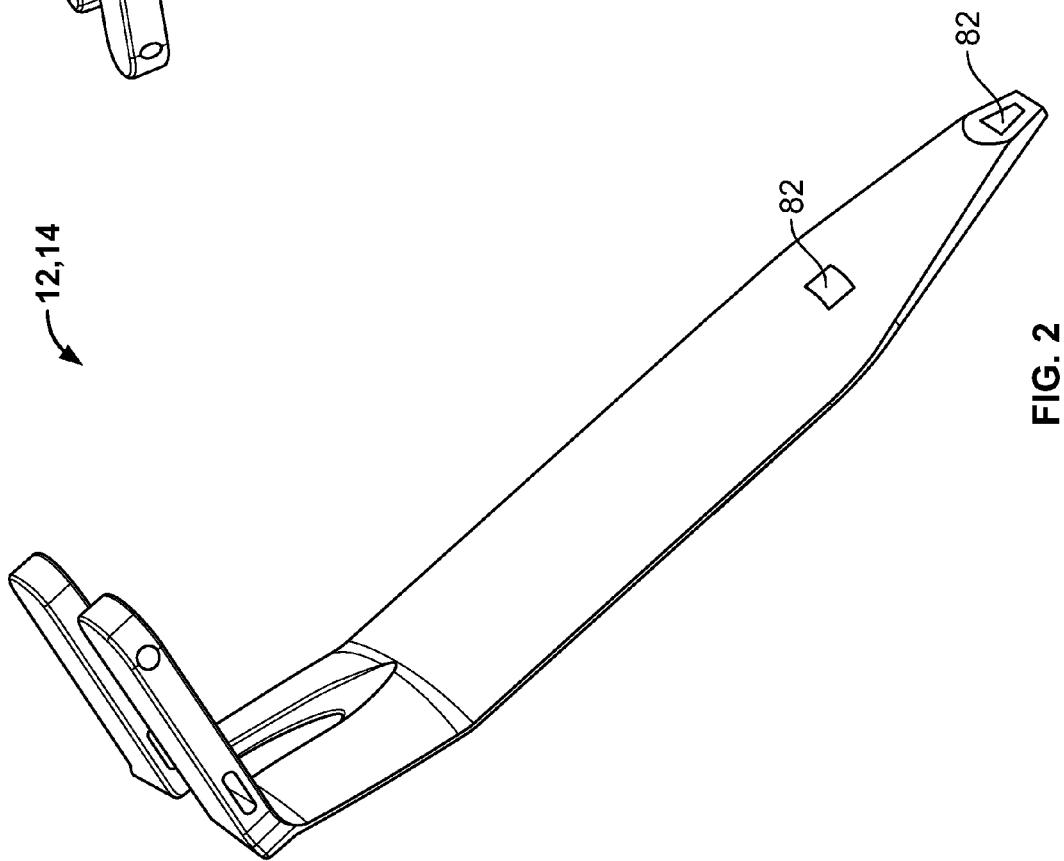

SURGICAL ACCESS SYSTEM AND RELATED METHODS

CROSS-REFERENCES TO RELATED APPLICATIONS

The present application is an application for US Letters Patent of and claims the benefit of priority from commonly owned and U.S. Provisional Patent Application Ser. No. 60/417,235 (filed Oct. 8, 2002), the entire contents of which is hereby expressly incorporated by reference into this disclosure as if set forth fully herein. The present application also incorporates by reference the following co-pending and co-assigned patent applications in their entireties (collectively, the "NeuroVision Applications"): PCT App. Ser. No. PCT/US02/22247, entitled "System and Methods for Determining Nerve Proximity, Direction, and Pathology During Surgery," filed on Jul. 11, 2002; PCT App. Ser. No. PCT/US02/30617, entitled "System and Methods for Performing Surgical Procedures and Assessments," filed on Sep. 25, 2002; PCT App. Ser. No. PCT/US02/35047, entitled "System and Methods for Performing Percutaneous Pedicle Integrity Assessments," filed on Oct. 30, 2002; PCT App. Ser. No. PCT/US03/02056, entitled "System and Methods for Determining Nerve Direction to a Surgical Instrument," filed Jan. 15, 2003.

BACKGROUND

I. Field

The present invention relates generally to systems and methods for performing surgical procedures and, more particularly, for accessing a surgical target site in order to perform surgical procedures.

II. Description of Related Art

A noteworthy trend in the medical community is the move away from performing surgery via traditional "open" techniques in favor of minimally invasive or minimal access techniques. Open surgical techniques are generally undesirable in that they typically require large incisions and high amounts of tissue displacement to gain access to the surgical target site, which produces concomitantly high amounts of pain, lengthened hospitalization (increasing health care costs), and high morbidity in the patient population. Less-invasive surgical techniques (including so-called "minimal access" and "minimally invasive" techniques) are gaining favor due to the fact that they involve accessing the surgical target site via incisions of substantially smaller size with greatly reduced tissue displacement requirements. This, in turn, reduces the pain, morbidity and cost associated with such procedures. The access systems developed to date, however, fail in various respects to meet all the needs of the surgeon population.

One drawback associated with prior art surgical access systems relates to the ease with which the operative corridor can be created, as well as maintained over time, depending upon the particular surgical target site. For example, when accessing surgical target sites located beneath or behind musculature or other relatively strong tissue (such as, by way of example only, the psoas muscle adjacent to the spine), it has been found that advancing an operative corridor-establishing instrument directly through such tissues can be challenging and/or lead to unwanted or undesirable effects (such as stressing or tearing the tissues). While certain efforts have been undertaken to reduce the trauma to tissue while creating an operative corridor, such as (by way of example only) the sequential dilation system of U.S. Pat. No. 5,792,044 to Foley et al., these attempts are nonetheless limited in their applicability based on the relatively narrow operative corridor. More specifically, based on the generally cylindrical nature of the so-called "working cannula," the degree to which instruments can be manipulated and/or angled within the cannula can be generally limited or restrictive, particularly if the surgical target site is a relatively deep within the patient.

Efforts have been undertaken to overcome this drawback, such as shown in U.S. Pat. No. 6,524,320 to DiPoto, wherein an expandable portion is provided at the distal end of a cannula for creating a region of increased cross-sectional area adjacent to the surgical target site. While this system may provide for improved instrument manipulation relative to sequential dilation access systems (at least at deep sites within the patient), it is nonetheless flawed in that the deployment of the expandable portion may inadvertently compress or impinge upon sensitive tissues adjacent to the surgical target site. For example, in anatomical regions having neural and/or vasculature structures, such a blind expansion may cause the expandable portion to impinge upon these sensitive tissues and cause neural and/or vasculature compromise, damage and/or pain for the patient.

This highlights yet another drawback with the prior art surgical access systems, namely, the challenges in establishing an operative corridor through or near tissue having major neural structures which, if contacted or impinged, may result in neural impairment for the patient. Due to the threat of contacting such neural structures, efforts thus far have largely restricted to establishing operative corridors through tissue having little or substantially reduced neural structures, which effectively limits the number of ways a given surgical target site can be accessed. This can be seen, by way of example only, in the spinal arts, where the exiting nerve roots and neural plexus structures in the psoas muscle have rendered a lateral or far lateral access path (so-called trans-psoas approach) to the lumbar spine virtually impossible. Instead, spine surgeons are largely restricted to accessing the spine from the posterior (to perform, among other procedures, posterior lumbar interbody fusion (PLIF)) or from the anterior (to perform, among other procedures, anterior lumbar interbody fusion (ALIF)).

Posterior-access procedures involve traversing a shorter distance within the patient to establish the operative corridor, albeit at the price of oftentimes having to reduce or cut away part of the posterior bony structures (i.e. lamina, facets, spinous process) in order to reach the target site (which typically comprises the disc space). Anterior-access procedures are relatively simple for surgeons in that they do not involve reducing or cutting away bony structures to reach the surgical target site. However, they are nonetheless disadvantageous in that they require traversing through a much greater distance within the patient to establish the operative corridor, oftentimes requiring an additional surgeon to assist with moving the various internal organs out of the way to create the operative corridor.

The present invention is directed at eliminating, or at least minimizing the effects of, the above-identified drawbacks in the prior art.

SUMMARY

The present invention accomplishes this goal by providing a novel access system and related methods which involve: (1) distracting the tissue between the patient's skin and the surgical target site to create an area of distraction (otherwise referred to herein as a "distraction corridor"); (2) retracting the distraction corridor to establish and maintain an operative corridor; and/or (3) detecting the existence of (and optionally the distance and/or direction to) neural structures before, during and after the establishment of the operative corridor through (or near) any of a variety of tissues having such neural structures which, if contacted or impinged, may otherwise result in neural impairment for the patient.

As used herein, "distraction" or "distracting" is defined as the act of creating a corridor (extending to a location at or near the surgical target site) having a certain cross-sectional area and shape ("distraction corridor"), and "retraction" or "retracting" is defined as the act of creating an operative corridor by increasing or maintaining the cross-sectional area of the distraction corridor (and/or modifying its shape) with at least one retractor blade such that surgical instruments can be passed through operative corridor to the surgical target site. It is expressly noted that, although described herein largely in terms of use in spinal surgery, the access system of the present invention is suitable for use in any number of additional surgical procedures, including those wherein tissue having significant neural structures must be passed through (or near) in order to establish an operative corridor.

According to one broad aspect of the present invention, the access system comprises a tissue distraction assembly and a tissue retraction assembly. The tissue distraction assembly (in conjunction with one or more elements of the tissue retraction assembly) is capable of, as an initial step, distracting a region of tissue between the skin of the patient and the surgical target site. The tissue retraction assembly is capable of, as a secondary step, being introduced into this distracted region to thereby define and establish the operative corridor. Once established, any of a variety of surgical instruments, devices, or implants may be passed through and/or manipulated within the operative corridor depending upon the given surgical procedure.

The tissue distraction assembly may include any number of components capable of performing the necessary distraction. By way of example only, the tissue distraction assembly may include a K-wire, an initial dilator of split construction, and one or more dilators of traditional (that is, non-split) construction for performing the necessary tissue distraction to receive the remainder of the tissue retractor assembly thereafter. One or more electrodes may be provided on one or more of the K-wire and dilator(s) to detect the presence of (and optionally the distance and/or direction to) neural structures during tissue distraction.

The tissue retraction assembly may include any number of components capable of performing the necessary retraction. By way of example only, the tissue retraction assembly may include one or more retractor blades extending proximally from the surgical target site for connection with a portion (more specifically, a pivot linkage assembly) of the speculum assembly. The retractor blades may be equipped with a mechanism for transporting or emitting light at or near the surgical target site to aid the surgeon's ability to visualize the surgical target site, instruments and/or implants during the given surgical procedure. According to one embodiment, this mechanism may comprise, but need not be limited to, providing one or more strands of fiber optic cable within the walls of the retractor blades such that the terminal (distal) ends are capable of emitting light at or near the surgical target site. According to another embodiment, this mechanism may comprise, but need not be limited to, constructing the retractor blades of suitable material (such as clear polycarbonate) and configuration such that light may be transmitted generally distally through the walls of the retractor blade light to shine light at or near the surgical target site. This may be performed by providing the retractor blades having light-transmission characteristics (such as with clear polycarbonate construction) and transmitting the light almost entirely within the walls of the retractor blade (such as by frosting or otherwise rendering opaque portions of the exterior and/or interior) until it exits a portion along the interior (or medially-facing) surface of the retractor blade to shine at or near the surgical target site. The exit portion may be optimally configured such that the light is directed towards the approximate center of the surgical target site and may be provided along the entire inner periphery of the retractor blade or one or more portions therealong.

The retractor blades may be optionally dimensioned to receive and direct a rigid shim element to augment the structural stability of the retractor blades and thereby ensure the operative corridor, once established, will not decrease or become more restricted, such as may result if distal ends of the retractor blades were permitted to "slide" or otherwise move in response to the force exerted by the displaced tissue. In a preferred embodiment, only the posterior and anterior retractor blades are equipped with such rigid shim elements, which are advanced into the disc space after the posterior and anterior retractor blades are positioned. The rigid shim elements are preferably oriented within the disc space such that they distract the adjacent vertebral bodies, which serves to restore disc height. They are also preferably advanced a sufficient distance within the disc space (preferably past the midline), which serves the dual purpose of preventing post-operative scoliosis and forming a protective barrier (preventing the migration of tissue (such as nerve roots) into the operative field and the inadvertent advancement of instruments outside the operative field).

According to yet another aspect of the present invention, any number of distraction assemblies and/or retraction assemblies (including but not limited to those described herein) may be equipped to detect the presence of (and optionally the distance and/or direction to) neural structures during the steps tissue distraction and/or retraction. To accomplish this, one or more stimulation electrodes are provided on the various components of the distraction assemblies and/or retraction assemblies, a stimulation source (e.g. voltage or current) is coupled to the stimulation electrodes, a stimulation signal is emitted from the stimulation electrodes as the various components are advanced towards the surgical target site, and the patient is monitored to determine if the stimulation signal causes muscles associated with nerves or neural structures within the tissue to innervate. If the nerves innervate, this indicates that neural structures may be in close proximity to the distraction and/or retraction assemblies.

This monitoring may be accomplished via any number of suitable fashions, including but not limited to observing visual twitches in muscle groups associated with the neural structures likely to found in the tissue, as well as any number of monitoring systems. In either situation (traditional EMG or surgeon-driven EMG monitoring), the access system of the present invention may advantageously be used to traverse tissue that would ordinarily be deemed unsafe or undesirable, thereby broadening the number of manners in which a given surgical target site may be accessed.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIGS. 2 and 3 are front and back views, respectively, of the posterior and anterior retractor blades 12, 14 shown in FIG. 1;

DETAILED DESCRIPTION

Figure 1:
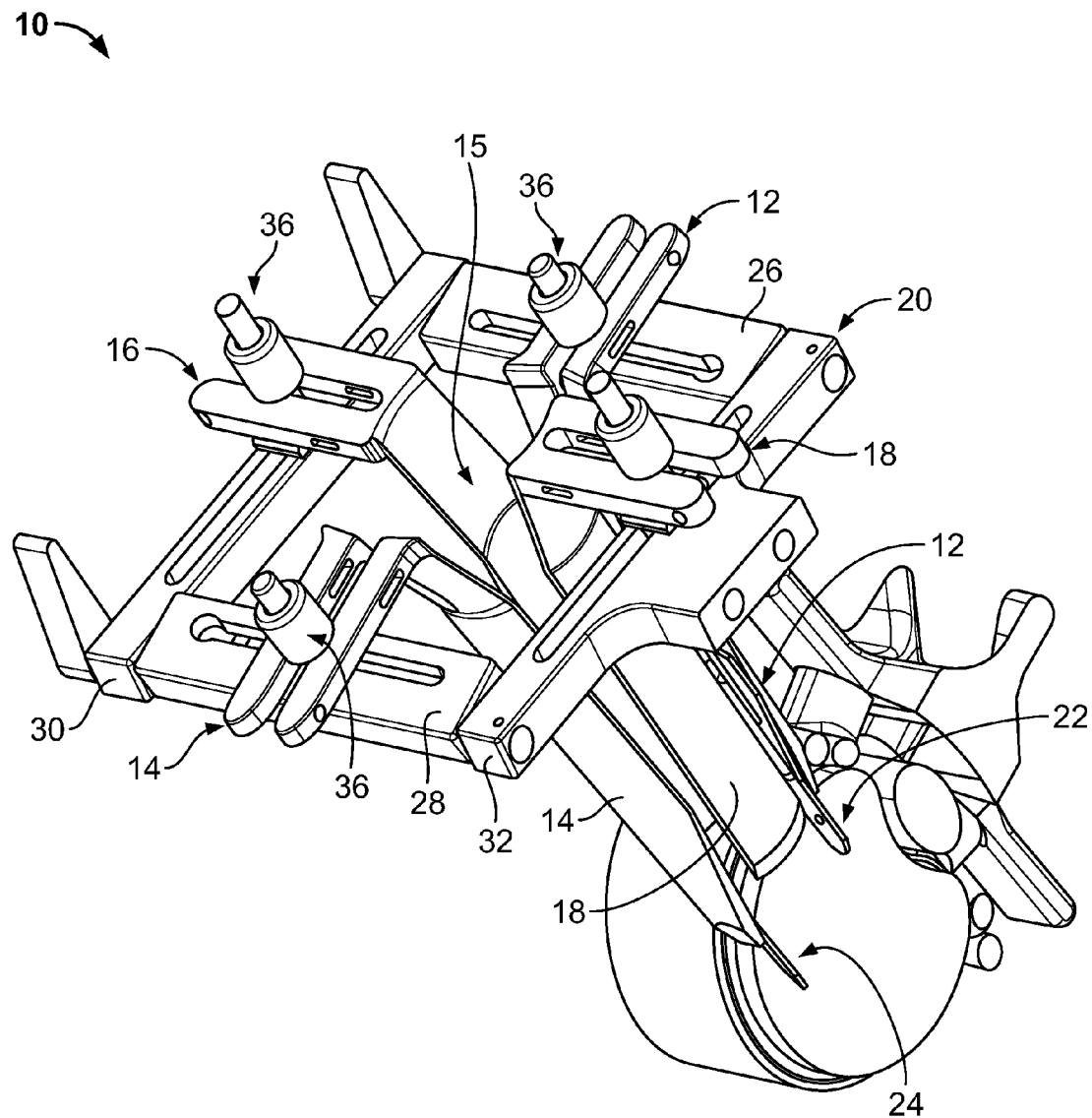
FIG. 1 is a perspective view of a tissue retraction assembly (in use) forming part of a surgical access system according to the present invention, including a posterior retractor blade 12, an anterior retractor blade 14, and two supplemental retractor blades 16, 18.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The surgical access system disclosed herein boasts a variety of inventive features and components that warrant patent protection, both individually and in combination.

It is furthermore to be readily understood that, although discussed below primarily within the context of spinal surgery, the surgical access system and related methods of the present invention may find applicability in any of a variety of surgical and/or medical applications such that the following description relative to the spine is not to be limiting of the overall scope of the present invention. Moreover, while described below employing the nerve monitoring features described above (otherwise referred to as "nerve surveillance") during spinal surgery, it will be appreciated that such nerve surveillance will not be required in all situations, depending upon the particular surgical target site (e.g. disk space, vertebral body, and/or internal organ) and surgical approach (e.g. lateral, posterior, anterior, and/or postero-lateral approaches to the spine).

The present invention is directed at a novel surgical access system and related methods which involve creating and maintaining an operative corridor to the surgical target site, and optionally detecting the existence of (and optionally the distance and/or direction to) neural structures before, during and/or after this process (including the steps of distraction and/or retraction).

Distraction followed by retraction is advantageous because it provides the ability to more easily position an operative corridor-establishing device through tissue that is strong, thick or otherwise challenging to traverse in order to access a surgical target site. The various distraction systems of the present invention are advantageous in that they provide an improved manner of atraumatically establishing a distraction corridor prior to the use of the retraction systems of the present invention. The various retractor systems of the present invention are advantageous in that they provide an operative corridor having improved cross-sectional area and shape (including customization thereof) relative to the prior art surgical access systems. Moreover, by optionally equipping the various distraction systems and/or retraction systems with one or more electrodes, an operative corridor may be established through (or near) any of a variety of tissues having such neural structures which, if contacted or impinged, may otherwise result in neural impairment for the patient.

The present invention involves accessing a surgical target site in a fashion less invasive than traditional "open" surgeries and doing so in a manner that provides access in spite of the neural structures required to be passed through (or near) in order to establish an operative corridor to the surgical target site. Generally speaking, the surgical access system of the present invention accomplishes this by providing a tissue distraction assembly and a tissue retraction assembly, both of which may be equipped with one or more electrodes for use in detecting the existence of (and optionally the distance and/or direction to) neural structures. These electrodes are preferably provided for use with a nerve surveillance system such as, by way of example, the type shown and described in the NeuroVision Applications referenced above, the entire contents of which are expressly incorporated by reference as if set forth herein in their entirety.

Generally speaking, this nerve surveillance is capable of detecting the existence of (and optionally the distance and/or direction to) neural structures during the distraction and retraction of tissue by detecting the presence of nerves by applying a stimulation signal to such instruments and monitoring the evoked EMG signals from the myotomes associated with the nerves being passed by the distraction and retraction systems of the present invention. In so doing, the system as a whole (including the surgical access system of the present invention) may be used to form an operative corridor through (or near) any of a variety of tissues having such neural structures, particularly those which, if contacted or impinged, may otherwise result in neural impairment for the patient. In this fashion, the access system of the present invention may be used to traverse tissue that would ordinarily be deemed unsafe or undesirable, thereby broadening the number of manners in which a given surgical target site may be accessed.

The tissue distraction assembly of the present invention (comprising a K-wire, an initial dilator, and a split-dilator disposed within the initial dilator) is employed to distract the tissues extending between the skin of the patient and a given surgical target site (preferably along the posterior region of the target intervertebral disc) such that, once distracted, the resulting void or distracted region within the patient is of sufficient size to accommodate the introduction of a posterior retractor blade forming part of a tissue retraction assembly of the present invention. This forms the posterior border of the resulting operative corridor. Following (or contemporaneous with) this, a posterior shim element (which is preferably slideably engaged with the posterior retractor blade) may be advanced such that a shim extension in positioned within the posterior region of the disc space. An anterior retractor blade may then be introduced (in generally abutting relation with the posterior retractor blade) and thereafter moved anteriorly to increase the AP (or "width") dimension of the operative corridor. Once in the appropriate anterior position, the anterior retractor blade may be locked in position and, thereafter, an anterior shim element advanced therealong for positioning a shim extension within the anterior of the disc space. The shim elements serve to distract the adjacent vertebral bodies (thereby restoring disc height), to form protective barriers (against the migration of tissue into (or instruments out of) the operative site), and to rigidly couple the posterior and anterior retractor blades in fixed relation relative to the vertebral bodies. First and second supplemental retractor blades (disposed caudal and cephalad) are also preferably employed to establish and maintain the "height" dimension of the operative corridor. Once established, any of a variety of surgical instruments, devices, or implants may be passed through and/or manipulated within the operative corridor depending upon the given surgical procedure.

FIG. 1 illustrates a tissue retraction assembly 10 forming part of a surgical access system according to the present invention. The retraction assembly 10 includes a posterior retractor blade 12, an anterior retractor blade 14, and supplemental retractor blades 16, 18, all of which are coupled to a mounting structure 20. Posterior and anterior retractor blades 12, 14 establish an AP (or "width") dimension of an operative corridor 15. Posterior retractor blade 12 and anterior retractor blade 14 are equipped with shim elements 22, 24, respectively. Shim elements 22, 24 serve to distract the adjacent vertebral bodies (thereby restoring disc height), form protective barriers (against the migration of tissue into (or instruments out of) the operative site), and rigidly couple the posterior and anterior retractor blades 12, 14 in fixed relation relative to the vertebral bodies. First and second supplemental retractor blades 16, 18 (disposed caudal and cephalad) establish and maintain the "height" dimension of the operative corridor 15.

Any number of suitable mounting units (not shown) may be employed to maintain the retraction assembly 10 in a fixed and rigid fashion relative to the patient. The mounting structure 20 may be coupled to any number of mechanisms for rigidly registering the mounting structure 20 in fixed relation to the operative site, such as through the use of an articulating arm mounted to the operating table. The mounting structure 20 includes posterior and anterior struts 26, 28 disposed in hinged relation to fixed strut members 30, 32. The hinged nature of struts 26, 28 allows the posterior and anterior retractor blades 12, 14 to be adjusted independently of one another. The proximal portion of each of the retractor blades 12-18 is preferably provided in a split or forked fashion to accommodate locking assemblies 36 for locking the position of the retractor blades 12-18 with respect to the mounting assembly 20.

Figure 4:
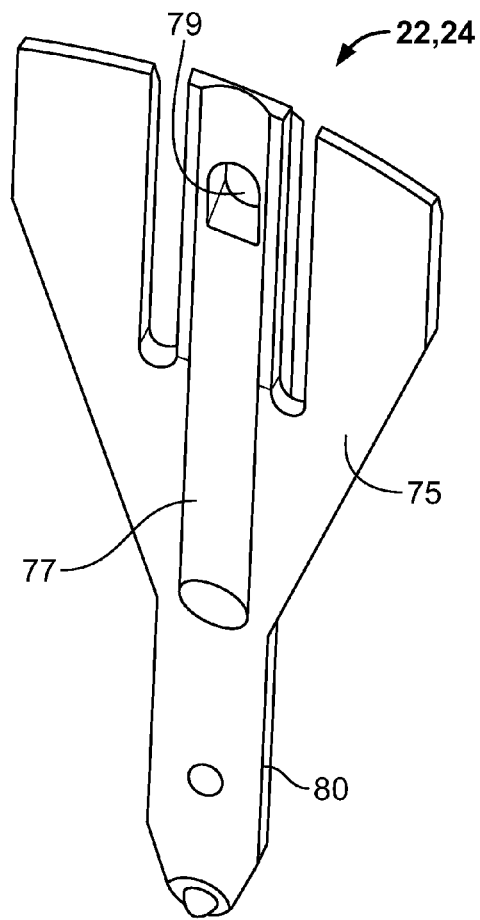
FIGS. 4 and 5 are front and back views, respectively, of shim element 22, 24 according to the present invention, dimensioned to be engaged with the inner surface of the posterior and anterior retractor blades of FIG. 1 for the purpose of positioning a shim extension 80 within the disc space.
Figure 5:
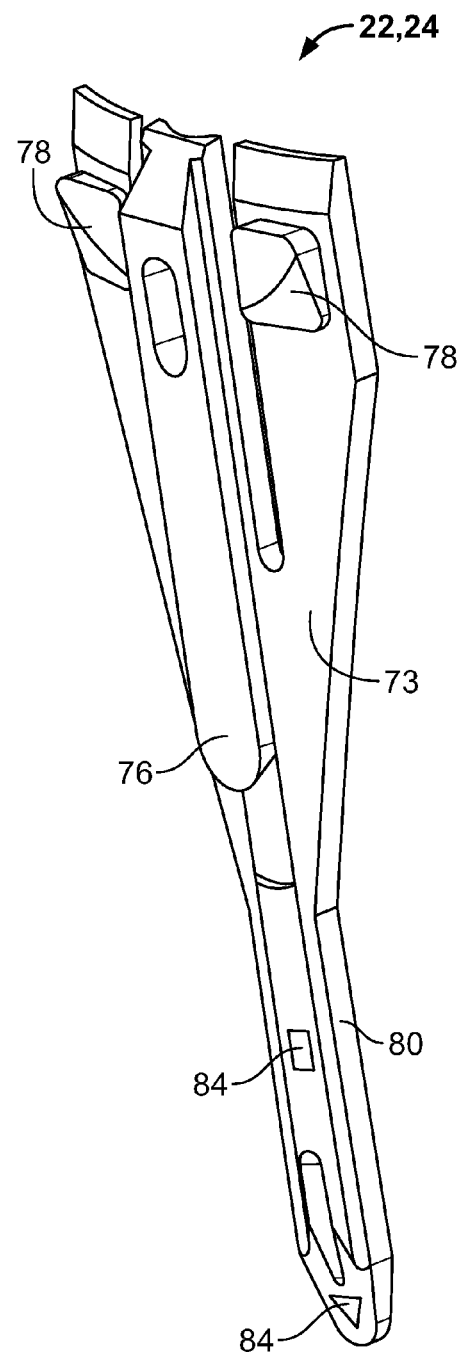

The retractor blades 12, 14 (FIGS. 2-3) are dimensioned to detachably couple with the shim elements 22, 24 (FIGS. 4-5), respectively. In one embodiment, shown best in FIG. 3, this is accomplished by providing the inner surface 72 of each retractor blade 12, 14 with an engagement groove 70 (having, by way of example, a female dove-tail configuration as shown) along the midline thereof and one or more recess 74 disposed at or near the distal end. As best seen in FIG. 5, the exterior surface 73 of each shim element 22, 24 is provided with an elongated engagement member 76 (having, by way of example, a male dove-tail configuration as shown) dimensioned to be slideably received within the engagement groove 70 of the retractor blades 12, 14, along with a pair of generally square-shaped engagement members 78 dimensioned to "snap" into the recesses 74 disposed at the distal ends of the retractor blades 12, 14.

Figure 6:
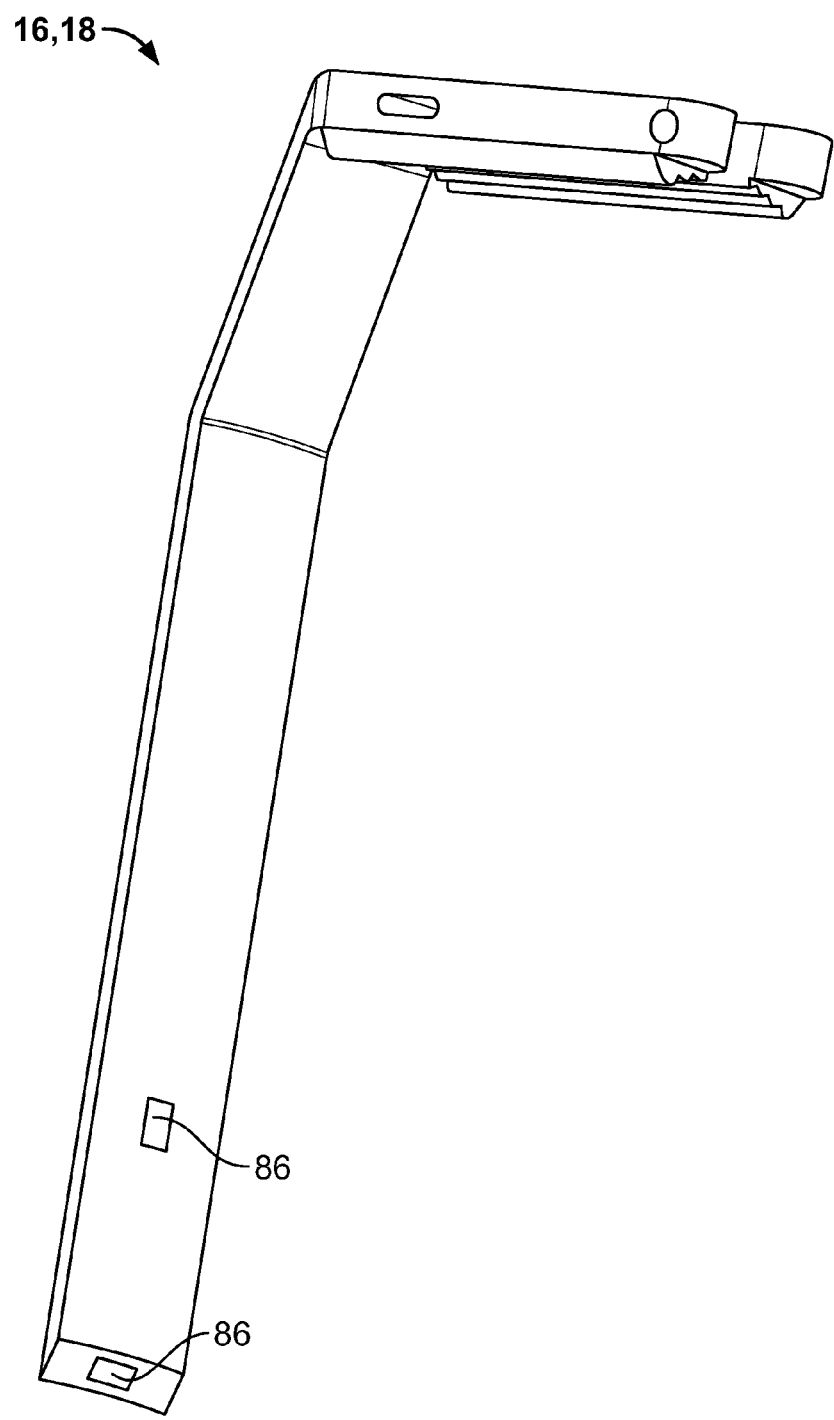
FIG. 6 is a perspective view illustrating the back of the supplemental retractor blades 16, 18 shown in FIG. 1 according to the present invention.

The inner surface 75 of each shim elements 22, 24 (FIG. 4) is provided with a generally concave region 77 having an aperture 79 formed therein for engagement with a shim introducer (shown generally in FIGS. 11 and 15) for the purpose of controlling the engagement between the shim elements 22, 24 and the retractor blades 12, 14, respectively, as well as the advancement of the distal regions 80 of the shim elements 22, 24 into the surgical target site (e.g. disc space). As best seen in FIGS. 2 and 5, the retractor blades 12, 14 and shim elements 22, 24 may be respectively provided with one or more electrodes 82, 84 for use in undertaking the nerve surveillance techniques described herein. The same is true for supplemental retractor blades 16, 18 (FIG. 6), which may also be provided with one or more electrodes 86 for use in undertaking the nerve surveillance techniques described herein.

The retractor blades 12-18, as well as the shim elements 22, 24 may optionally be equipped with any number of different mechanisms for transporting or emitting light at or near the surgical target site to aid the surgeon's ability to visualize the surgical target site, instruments and/or implants during the given surgical procedure. For example, one or more strands of fiber optic cable may be coupled to these components such that light may be delivered from a light source and selectively emitted into the operative corridor and/or the surgical target site.

This may be accomplished, by way of example only, by constructing the retractor blades 12-18 and/or shim elements 22, 24 of suitable material (such as clear polycarbonate) and configuration such that light may be transmitted generally distally through a light exit region formed along the entire inner periphery thereof and located in the general vicinity as the operative corridor 15. This may be performed by providing the retractor blades 12-18 and/or the shim elements 22, 24 with light-transmission characteristics (such as with clear polycarbonate construction) and transmitting the light almost entirely within the walls of the retractor blades 12-18 and/or shim elements 22, 24 (such as by frosting or otherwise rendering opaque portions of the exterior and/or interior and coupling the light source thereto such as via a port) until it exits a portion along the interior surface thereof to shine at or near the surgical target site.

In one embodiment, a variety of sets of retractor blades 12-18 and/or shim elements 22, 24 may be provided, each having a different length to account for any number of possible surgical target sites and/or anatomical configurations. In a further embodiment, each set of retractor blades 12-18 and/or shim elements 22, 24 may be marked or color-coded to aid in indicating to the surgeon the particular length of the blade 12-18 and/or shim element 22, 24 (and/or extension 80 of the shim elements 22, 24) and/or the depth of the surgical target site.

The retractor blades 12-18 and shim elements 22, 24 may be constructed from any number of materials suitable for medical applications, including but not limited to plastics, metals, ceramics or any combination thereof. Depending on the construction, some or all of these devices may be disposable (i.e. single use) and/or reusable (i.e. multi-use).

Figure 7:
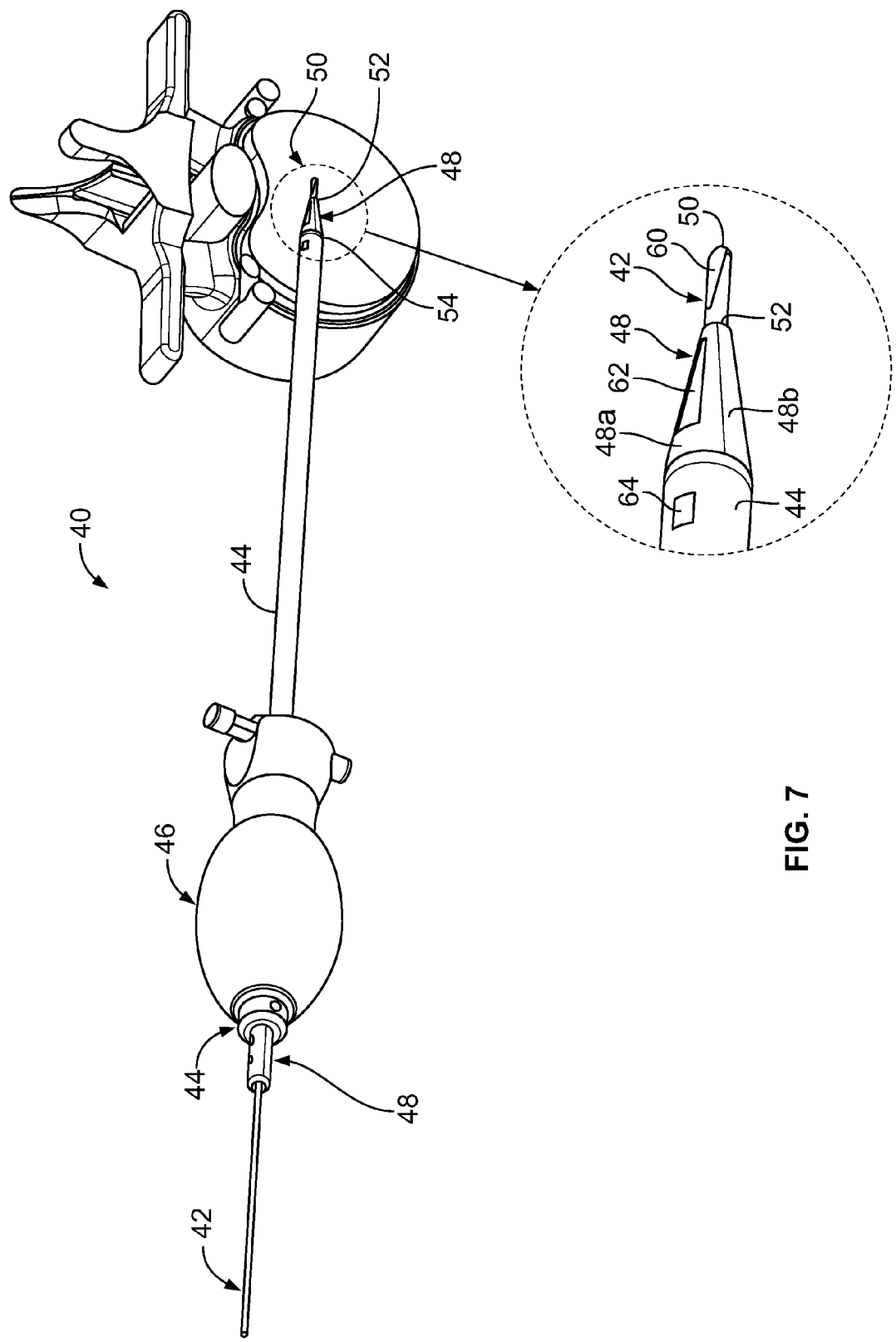
FIG. 7 is a perspective view illustrating the components and use of an initial distraction assembly 40 (i.e. K-wire 42, an initial dilating cannula 44 with handle 46, and a split-dilator 48 housed within the initial dilating cannula 44) forming part of the surgical access system according to the present invention, for use in distracting to a surgical target site (e.g. disk space)

FIG. 7 illustrates an initial distraction assembly 40 forming part of the surgical access system according to the present invention. The initial tissue distraction assembly 40 is employed to perform an initial distraction of tissue from the skin of the patient down to or near the surgical target site, prior to the introduction of the tissue retraction assembly 10 shown and described above with reference to FIGS. 1-6. By way of example, this is accomplished by providing the initial distraction assembly 40 as including a K-wire 42, an initial dilating cannula 44 with handle 46, and a split-dilator 48 housed within the initial dilating cannula 44. The initial tissue distraction assembly 40 may be constructed from any number of materials suitable for medical applications, including but not limited to plastics, metals, ceramics or any combination thereof. Depending on the construction, some or all of the tissue distraction assembly 40 may be disposable (i.e. single use) and/or reusable (i.e. multi-use). As will be discussed below in greater detail), the K-wire 42, initial dilating cannula 44, and split-dilator 48 may be provided with electrodes 60, 62, 64, respectively, for the purpose of determining the location of nerves or neural structures relative to these components as they are advanced towards or positioned at or near the surgical target site.

The K-wire 42 is preferably constructed having generally narrow diameter (such as, by way of example only, 1.5 mm) and sufficient rigidity and strength such that it can pierce the skin of the patient and be advanced through the intervening tissue to reach the surgical target site. The K-wire 42 also preferably includes indicia for determining the distance between a distal end thereof and the skin of the patient. The split-dilator 48 and dilating cannula 44 are inner and outer dilating elements, respectively, capable of being simultaneously introduced over the K-wire 42 for the purpose of further distracting the tissue previously distracted by the K-wire 42.

The split-dilator 48 is preferably constructed having an inner diameter approximating the diameter of the K-wire 42 (such as, by way of example only, 1.5 mm), an outer diameter of increased dimension (such as, by way of example only, 6.5 mm), and indicia for determining the distance between a distal end 52 and the skin of the patient. The initial dilating cannula 44 is similarly preferably constructed having an inner diameter approximating the outer diameter of the split-dilator 48 (such as, by way of example only, 6.5 mm), an outer diameter of increased dimension (such as, by way of example only, 7.5 mm), and indicia for determining the distance between a distal end 54 and the skin of the patient. The respective lengths of the K-wire 42, dilating cannula 44, and split-dilator 48 may vary depending upon the given surgical target site (that is, the "depth" of the surgical target site within the patient). It will be similarly appreciated that the diameters and dimensions for these elements may also vary depending upon the particular surgical procedure. All such surgically appropriate variations (length, diameter, etc. . . . ) are contemplated as falling within the scope of the present invention.

Figure 8:
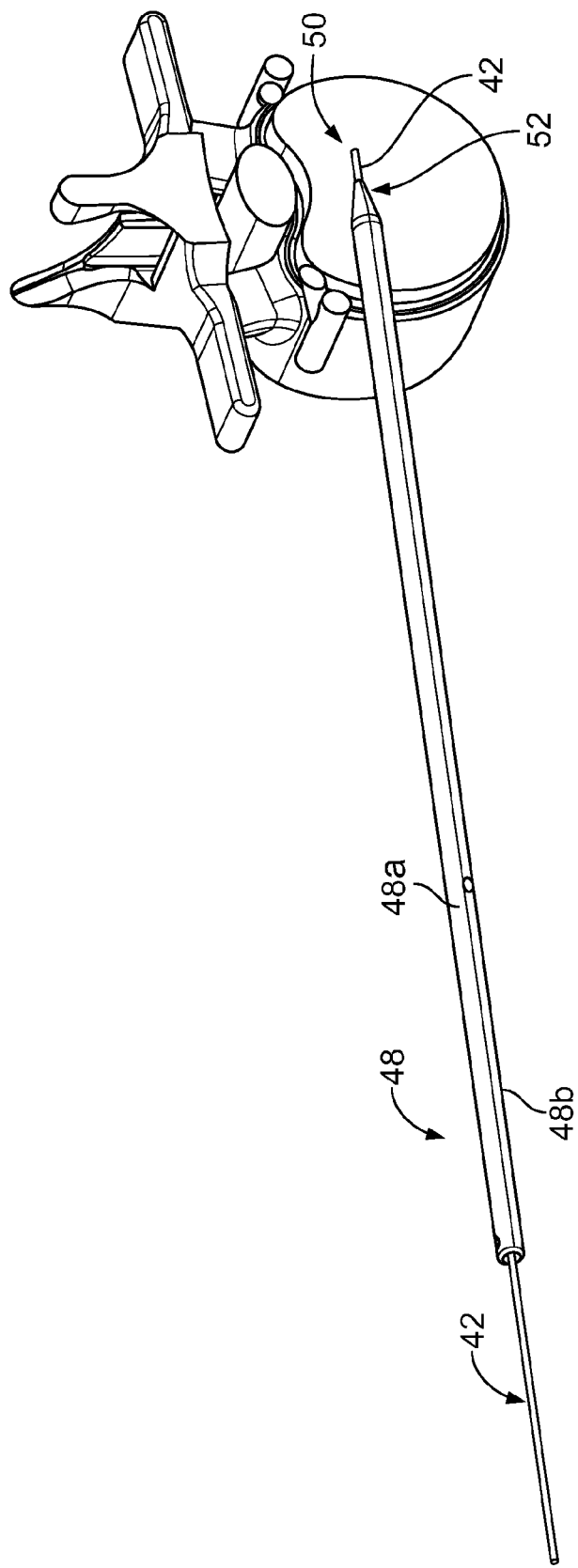
FIG. 8 is a perspective view illustrating the K-wire 42 and split-dilator 48 of the initial distraction assembly 40 with the initial dilating cannula 44 and handle 46 of FIG. 7 removed.
Figure 9:
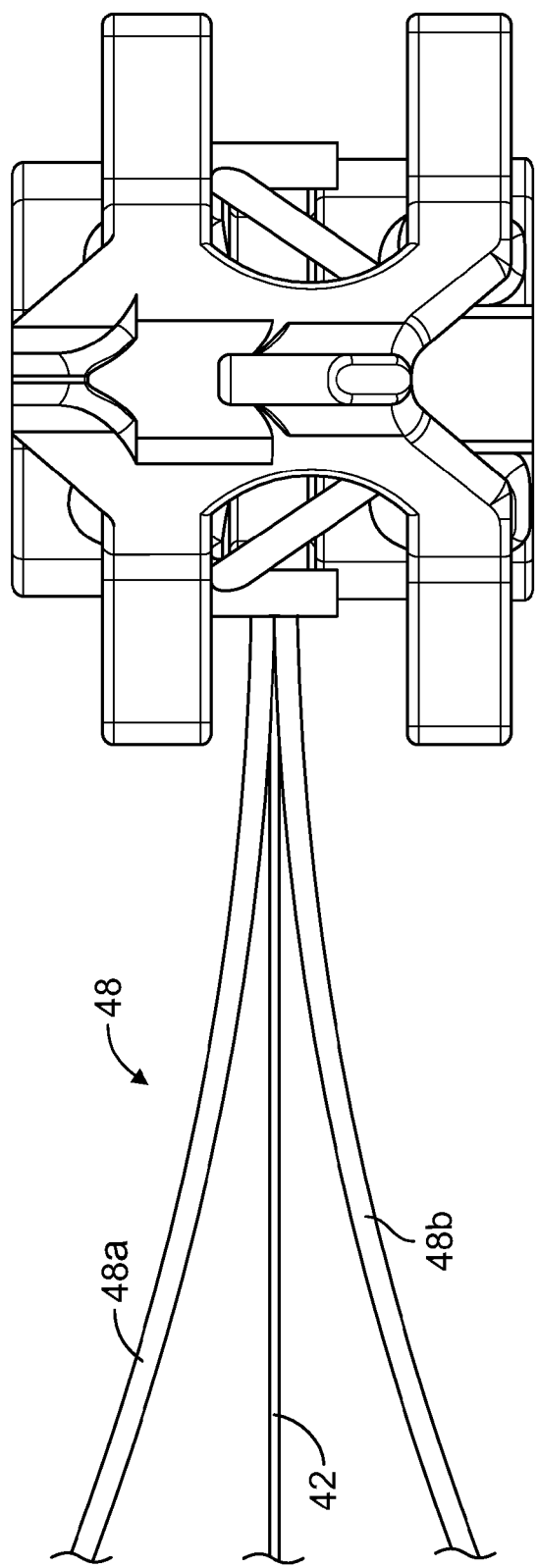
FIG. 9 is a posterior view of the vertebral target site illustrating the split-dilator 48 of the present invention in use distracting in a generally cephalad-caudal fashion according to one aspect of the present invention.

In use, the K-wire 42 and split-dilator 48 are disposed within the initial dilating cannula 44 and the entire assembly 40 advanced through the tissue towards the surgical target site (e.g. disk space) as shown in FIG. 7. After the initial dilating assembly 40 is advanced such that the distal ends of the split-dilator 48 and initial dilating cannula 44 are positioned within the disc space (FIG. 7), the initial dilator 44 and handle 46 are removed (FIG. 8) to thereby leave the split-dilator 48 and K-wire 42 in place. As shown in FIG. 9, the split-dilator 48 is thereafter split such that the respective halves 48a, 48b are separated from one another to distract tissue in a generally cephalad-caudal fashion relative to the target site. The split dilator 48 may thereafter be relaxed (allowing the dilator halves 48a, 48b to come together) and rotated such that the dilator halves 48a, 48b are disposed in the anterior-posterior plane. Once rotated in this manner, the dilator halves 48a, 48b are again separated to distract tissue in a generally anterior-posterior fashion.

Figure 10:
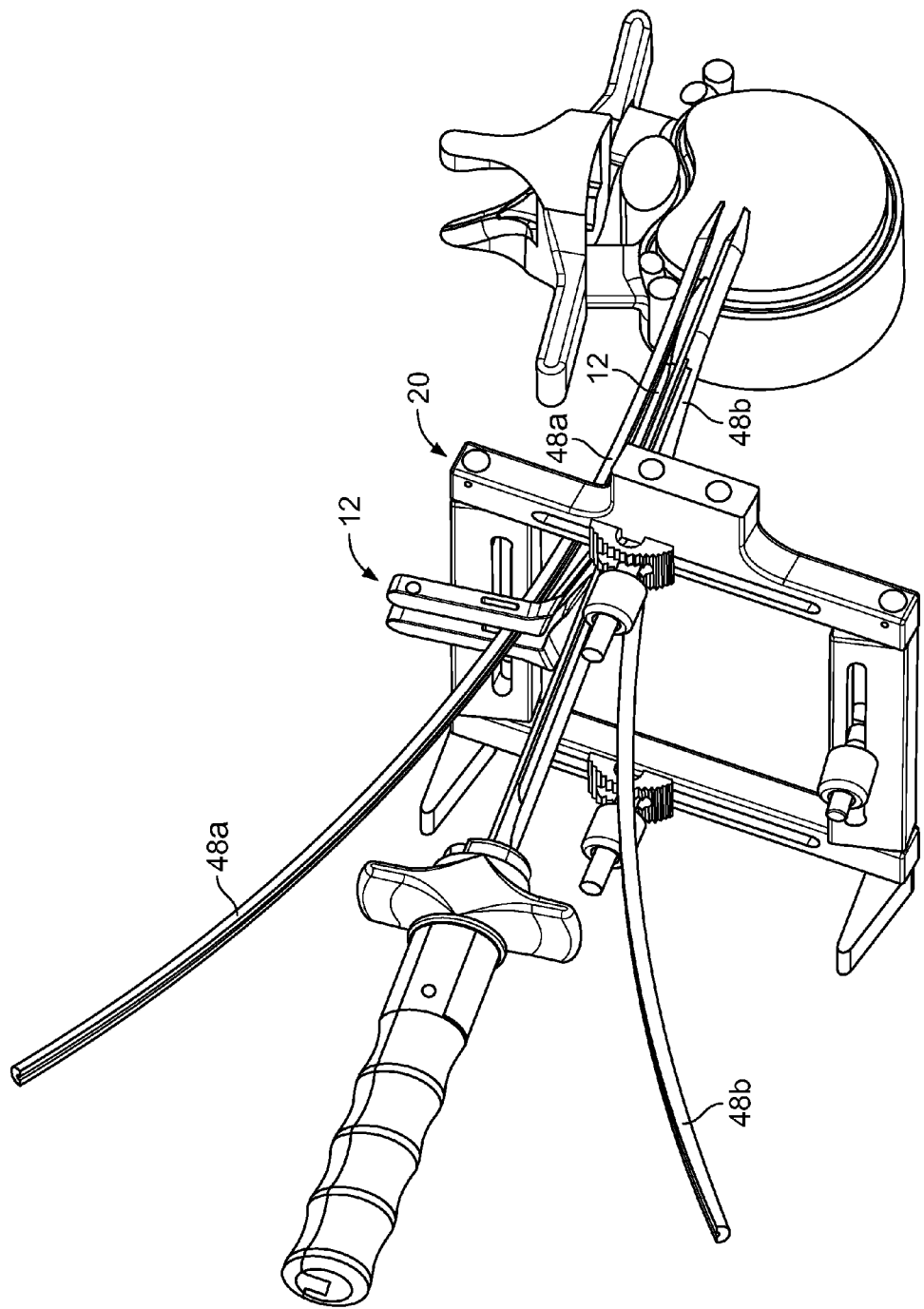
FIG. 10 is a perspective view illustrating the split-dilator 48 of the present invention in use distracting in a generally posterior-anterior fashion according to another aspect of the present invention and in use with a posterior retractor blade 12 forming part of the retractor assembly 10 of the present invention.
Figure 11:
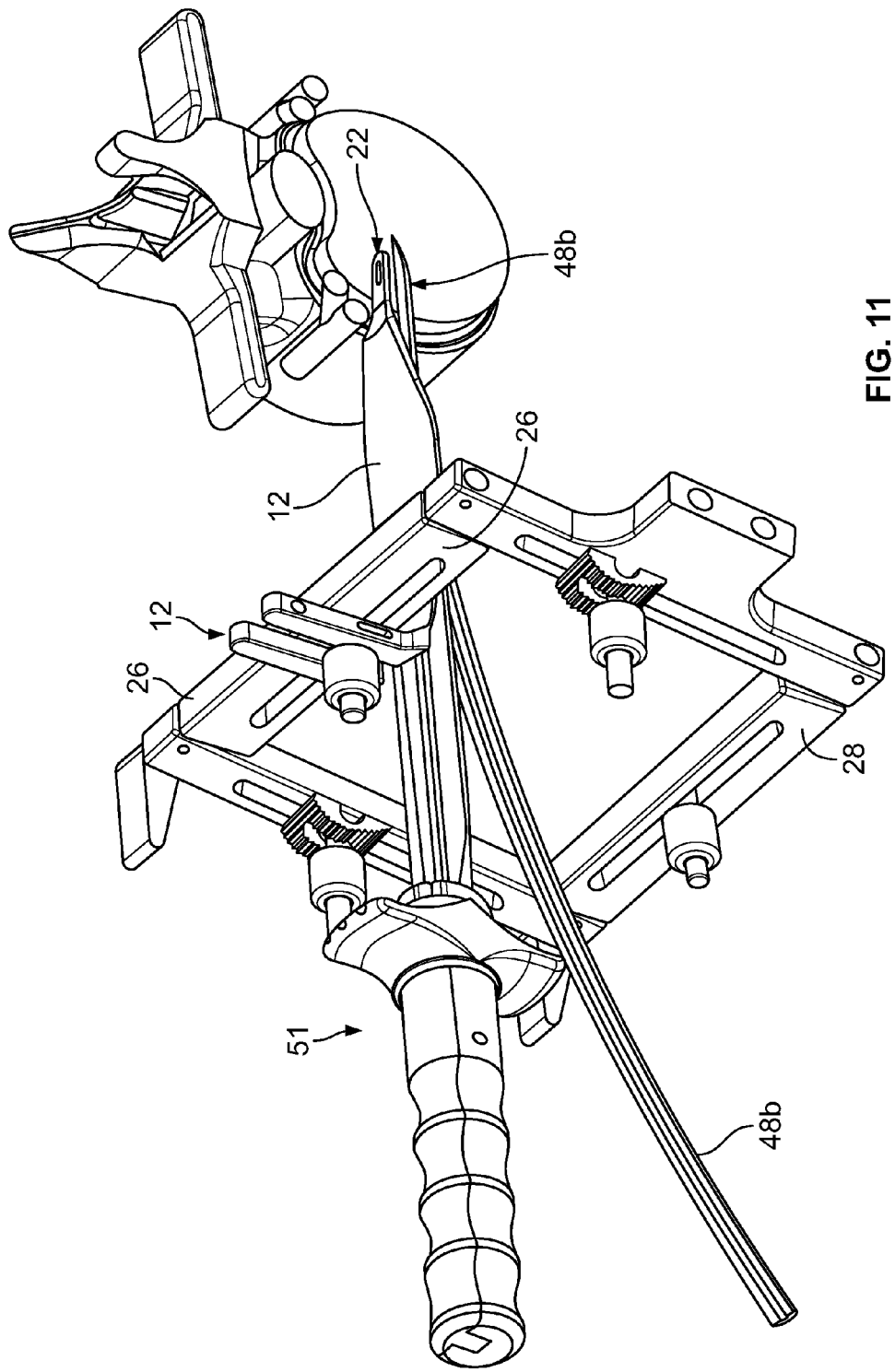
FIG. 11 is a perspective view illustrating a shim introducer 51 introducing the posterior shim element 22 such that the shim extension 80 is positioned within the disc space.
Figure 12:
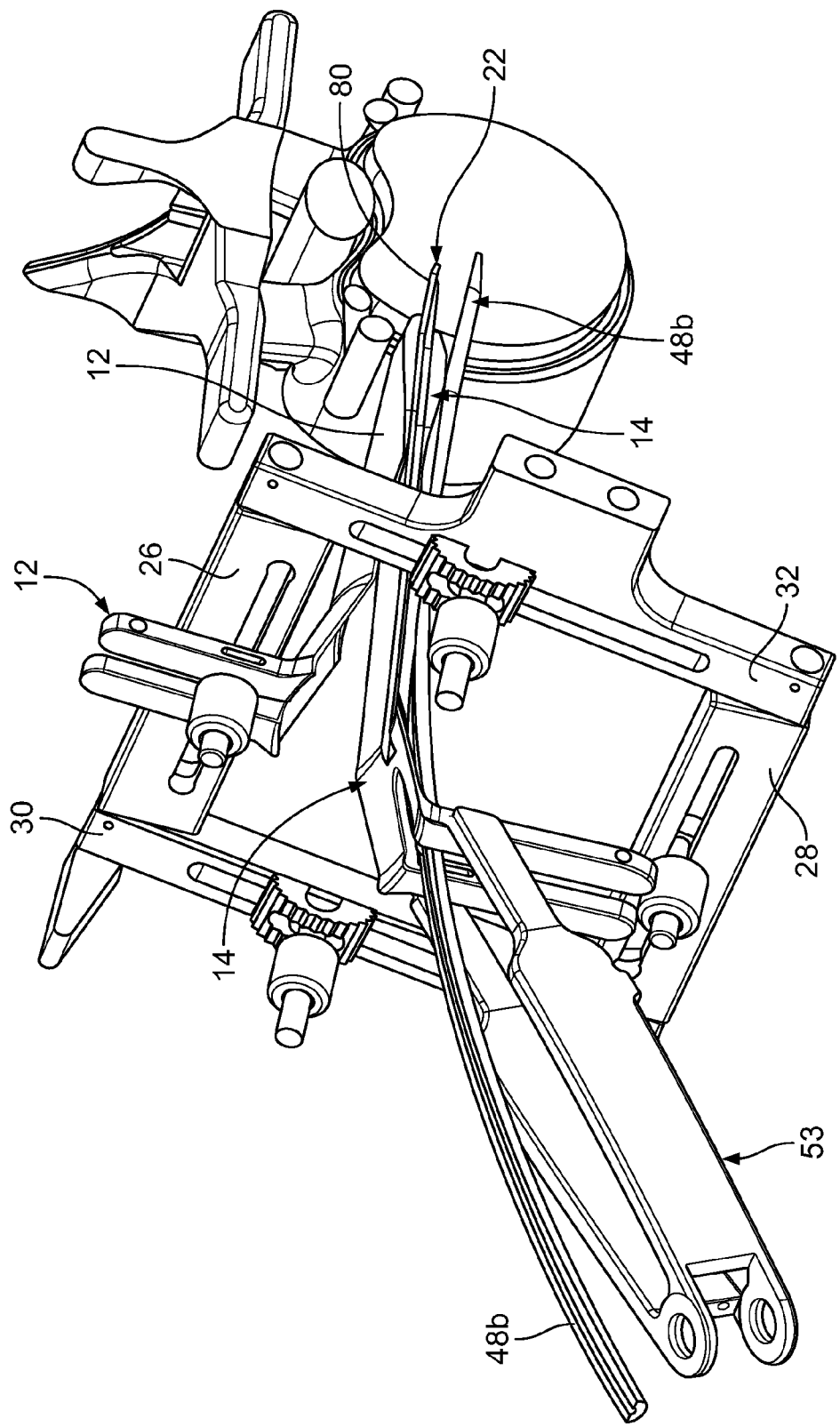
FIG. 12 is a perspective view illustrating an anterior retractor blade 14 forming part of the retractor assembly 10 of the present invention being introduced with a gripping assembly 53 in association with the anterior half 48b of the split dilator 48 of the present invention.
Figure 14:
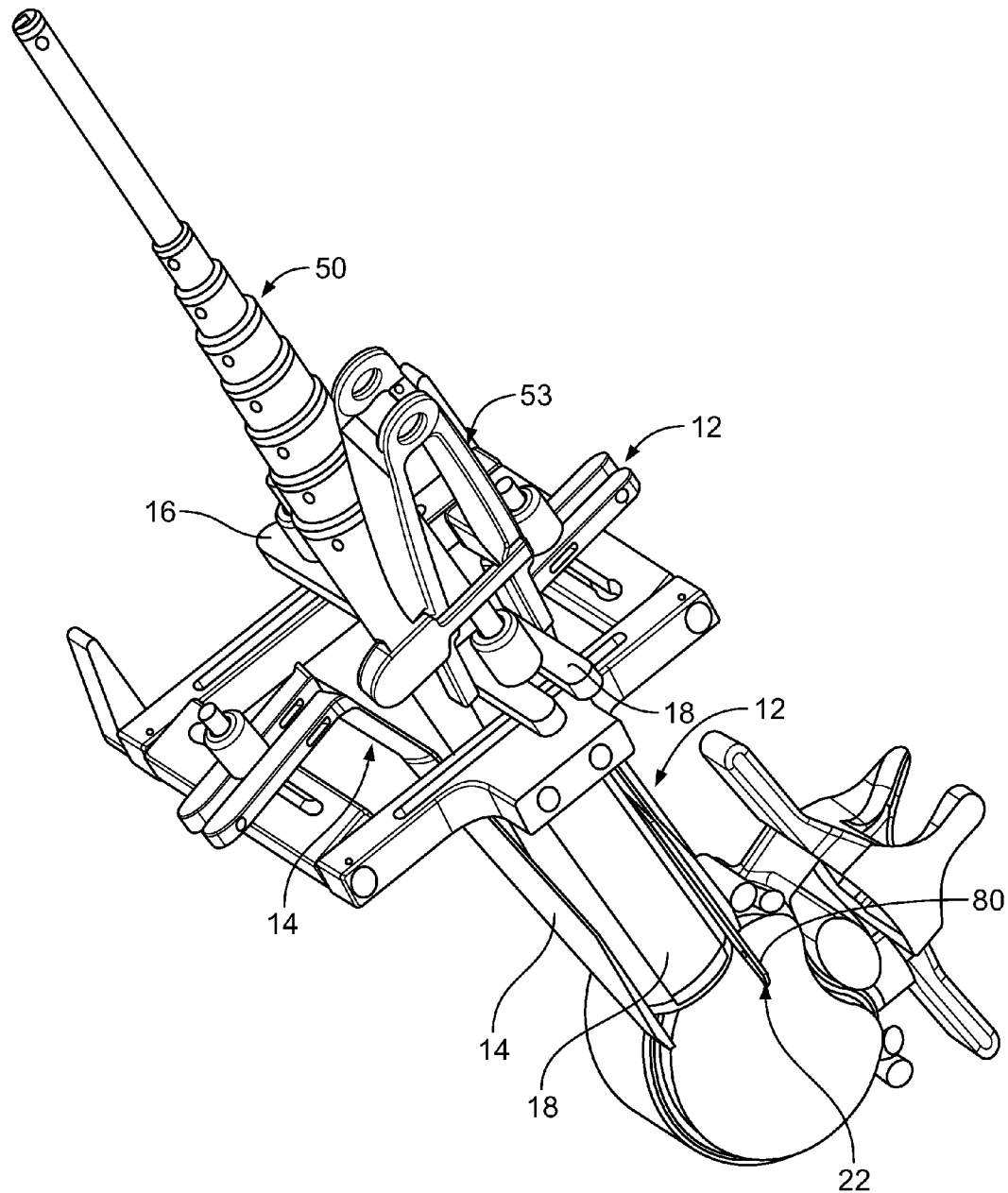
FIG. 14 is a perspective view illustrating the introduction of supplemental retractor blades 16, 18 according to the present invention.

As shown in FIG. 10, the posterior retractor blade 12 is thereafter advanced along the posterior half 48a of the split dilator 48. At this point, the posterior shim element 22 (FIGS. 4-5) may be advanced along the posterior retractor blade 12 (FIGS. 2-3) such that the shim extension 80 (distal end) is positioned in the posterior region of the disc space as shown in FIG. 11 (with posterior half 48a of the split dilator 48 removed). The anterior retractor blade 14 may thereafter be advanced along the anterior half 48b of the split dilator 48 as shown in FIG. 12. At this point, secondary distraction may be undertaken according to the present invention by removing the anterior half 48b of the split dilator 48 and introducing a plurality of sequentially dilating cannula 50 between the posterior retractor blade 12 and the anterior retractor blade 14 as shown in FIG. 14. This serves to move the anterior retractor blade 14 anteriorly from the posterior retractor blade 12.

Figure 15:
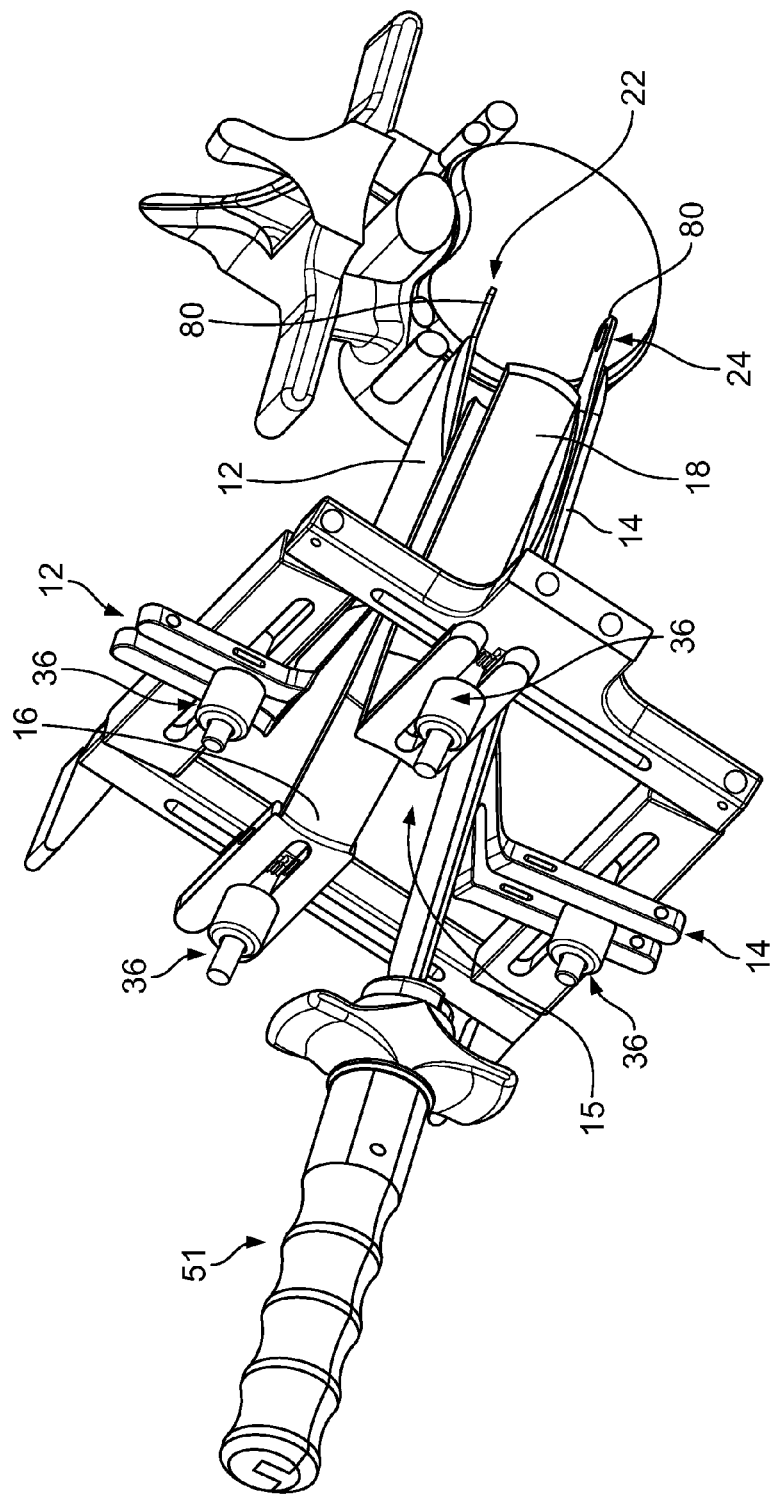
FIG. 15 is a perspective view illustrating a shim introducer 51 introducing the anterior shim element 24 such that the shim extension 80 is positioned within the disc space.

The retraction of the present invention is performed by expanding, modifying, and/or maintaining the distraction corridor to establish and/or maintain an operative corridor to the surgical target site. As shown in FIG. 15, according to one embodiment, this is accomplished by introducing the anterior shim element 24 along the anterior retractor blade 14 such that the shim extension 80 (distal region thereof) extends into the anterior region of the disc space. Supplemental retractor blades 16-18 (FIG. 6) may also optionally be introduced to define the cephalad and caudal sides of the operative corridor 15 as shown in FIGS. 14-15. Once positioned as such, the retractor blades 12, 14 and supplemental retractor blades 16, 18 may be locked in a position relative to the mounting structure 20 by tightening the respective nuts of the locking assemblies 36.

The retraction assembly 10 of the present invention, and in particular the shim extensions 80 of the posterior and anterior shim elements 22, 24 serve to prevent the ingress of unwanted or sensitive biological structures (e.g., nerve roots and/or vasculature) into the surgical target site, as well as prevent instruments from passing outside the surgical target site and contacting surrounding tissues or structures. Once established, any of a variety of surgical instruments, devices, or implants may be passed through and/or manipulated within the operative corridor 15 depending upon the given surgical procedure.

According to yet another aspect of the present invention, any number of distraction components and/or retraction components (including but not limited to those described herein) may be equipped to detect the presence of (and optionally the distance and/or direction to) neural structures during the steps tissue distraction and/or retraction. This is accomplished by employing the following steps: (1) one or more stimulation electrodes are provided on the various distraction and/or retraction components; (2) a stimulation source (e.g. voltage or current) is coupled to the stimulation electrodes; (3) a stimulation signal is emitted from the stimulation electrodes as the various components are advanced towards or maintained at or near the surgical target site; and (4) the patient is monitored to determine if the stimulation signal causes muscles associated with nerves or neural structures within the tissue to innervate. If the nerves innervate, this may indicate that neural structures may be in close proximity to the distraction and/or retraction components.

Neural monitoring may be accomplished via any number of suitable fashions, including but not limited to observing visual twitches in muscle groups associated with the neural structures likely to found in the tissue, as well as any number of monitoring systems, including but not limited to any commercially available "traditional" electromyography (EMG) system (that is, typically operated by a neurophysiologist. Such monitoring may also be carried out via the surgeon-driven EMG monitoring system shown and described in the following commonly owned and co-pending "NeuroVision Applications" incorporated by reference into this disclosure above. In any case (visual monitoring, traditional EMG and/or surgeon-driven EMG monitoring), the access system of the present invention may advantageously be used to traverse tissue that would ordinarily be deemed unsafe or undesirable, thereby broadening the number of manners in which a given surgical target site may be accessed.

Figure 16:
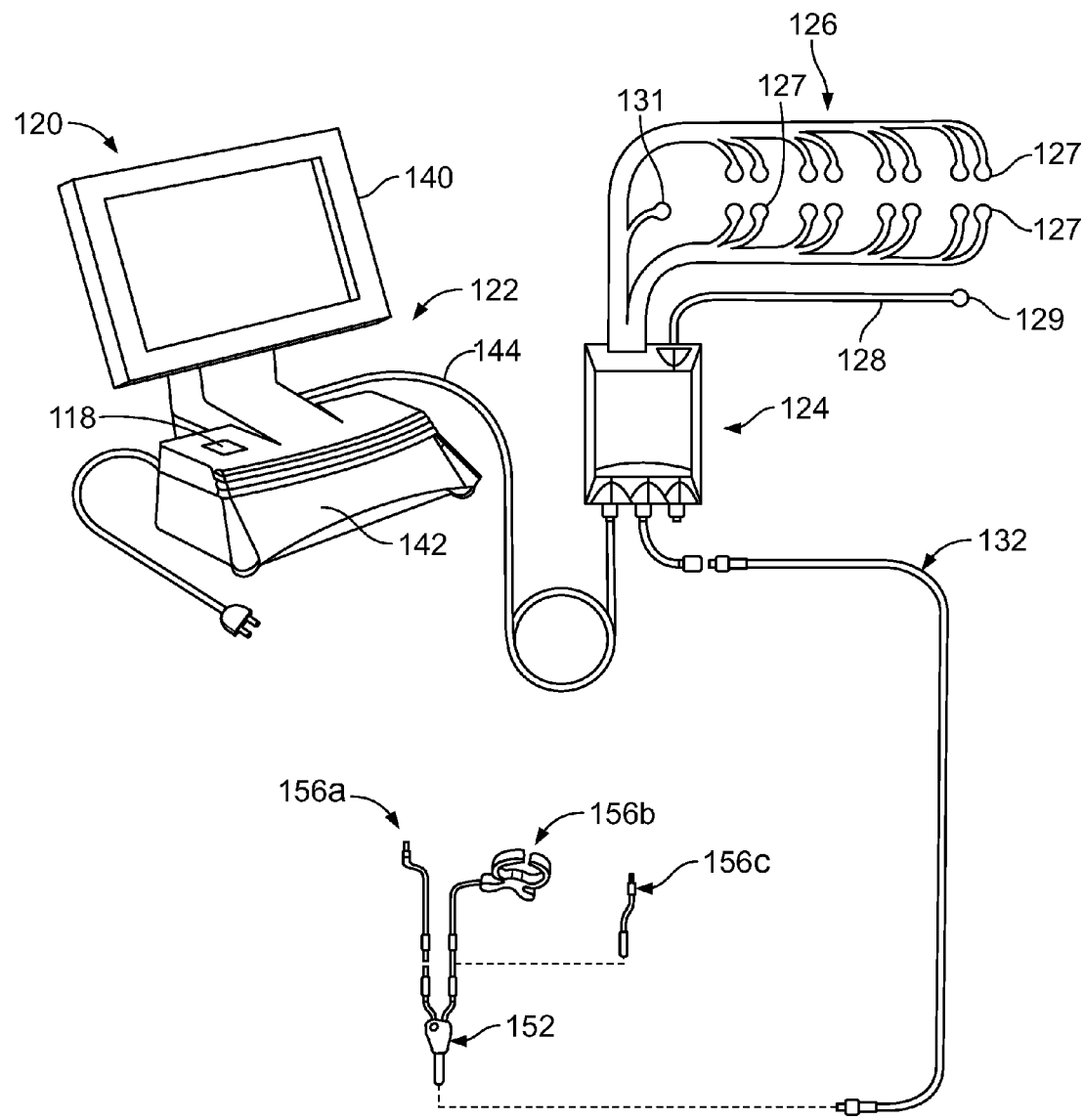
FIG. 16 is a perspective view of an exemplary nerve monitoring system capable of performing nerve monitoring before, during and after the creating of an operative corridor to a surgical target site using the surgical access system in accordance with the present invention.
Figure 17:
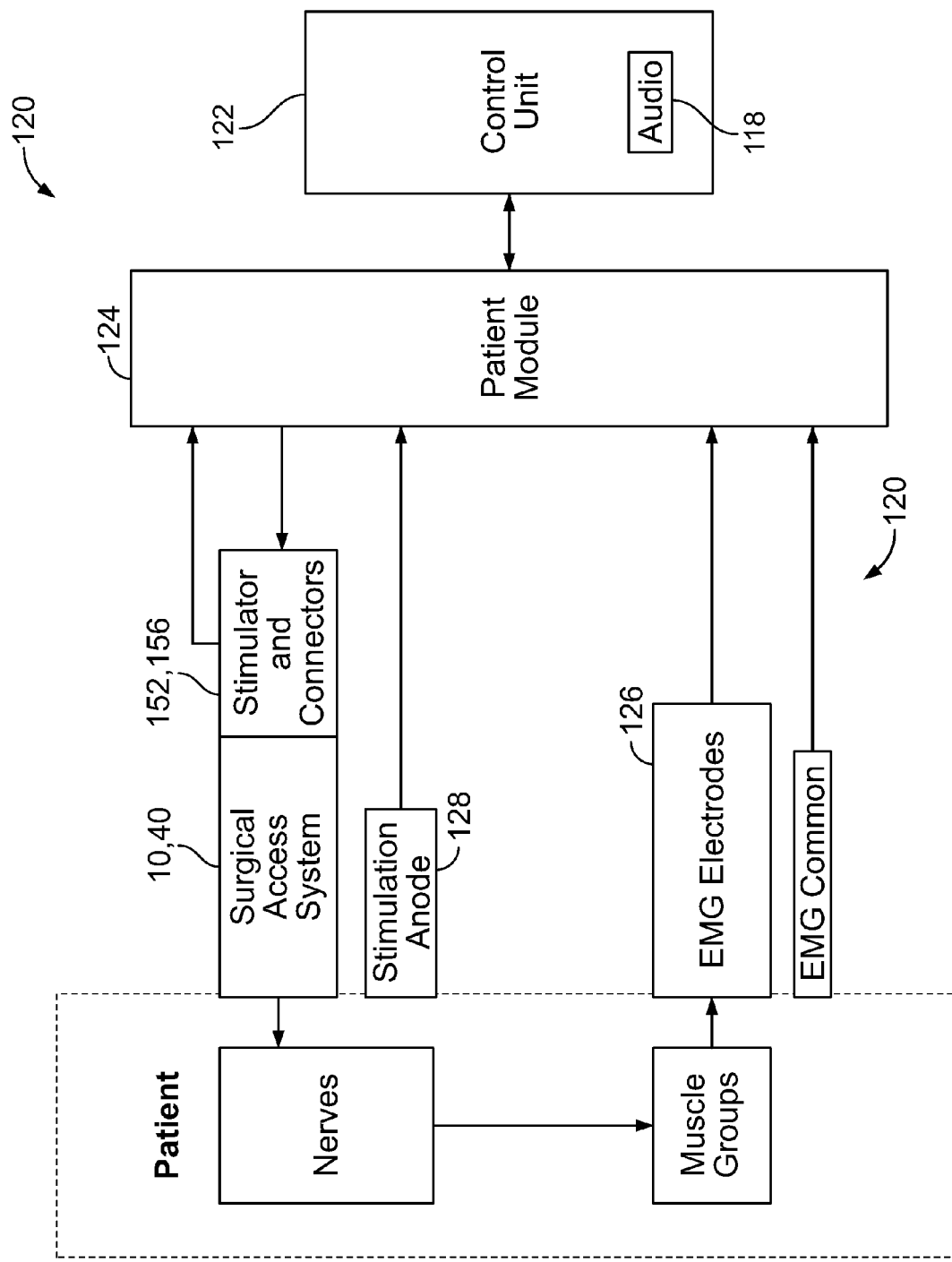
FIG. 17 is a block diagram of the nerve monitoring system shown in FIG. 16.

FIGS. 16-17 illustrate, by way of example only, a monitoring system 120 of the type disclosed in the NeuroVision Applications suitable for use with the surgical access system of the present invention. The monitoring system 120 includes a control unit 122, a patient module 124, and an EMG harness 126 and return electrode 128 coupled to the patient module 124, and a cable 132 for establishing electrical communication between the patient module 124 and the surgical access system of the present invention. More specifically, this electrical communication can be achieved by providing, by way of example only, a hand-held stimulation controller 152 capable of selectively providing a stimulation signal (due to the operation of manually operated buttons on the hand-held stimulation controller 152) to one or more connectors 156a, 156b, 156c. The connectors 156a, 156b, 156c are suitable to establish electrical communication between the hand-held stimulation controller 152 and (by way of example only) the stimulation electrodes on the K-wire 42, the dilating cannula 44, the split-blade dilator 48, the retractor blades 12-18, and/or the shim elements 22, 24 (collectively "Surgical Access Instruments").

In order to use the monitoring system 120, then, these Surgical Access Instruments must be connected to the connectors 156a, 156b and/or 156c, at which point the user may selectively initiate a stimulation signal (preferably, a current signal) from the control unit 122 to a particular Surgical Access Instruments. Stimulating the electrode(s) on these Surgical Access Instruments before, during and/or after establishing operative corridor will cause nerves that come into close or relative proximity to the Surgical Access Instruments to depolarize, producing a response in a myotome associated with the innervated nerve.

The control unit 122 includes a touch screen display 140 and a base 142, which collectively contain the essential processing capabilities (software and/or hardware) for controlling the monitoring system 120. The control unit 122 may include an audio unit 118 that emits sounds according to a location of a Surgical Access Instrument with respect to a nerve. The patient module 124 is connected to the control unit 122 via a data cable 144, which establishes the electrical connections and communications (digital and/or analog) between the control unit 122 and patient module 124. The main functions of the control unit 122 include receiving user commands via the touch screen display 140, activating stimulation electrodes on the surgical access instruments, processing signal data according to defined algorithms, displaying received parameters and processed data, and monitoring system status and report fault conditions. The touch screen display 140 is preferably equipped with a graphical user interface (GUI) capable of communicating information to the user and receiving instructions from the user. The display 140 and/or base 142 may contain patient module interface circuitry (hardware and/or software) that commands the stimulation sources, receives digitized signals and other information from the patient module 124, processes the EMG responses to extract characteristic information for each muscle group, and displays the processed data to the operator via the display 140.

In one embodiment, the monitoring system 120 is capable of determining nerve direction relative to one or more of the K-wire 42, dilating cannula 44, split-retractor 48, retractor blades 12-18, and/or the shim elements 22, 24 before, during and/or following the creation of an operative corridor to a surgical target site. Monitoring system 120 accomplishes this by having the control unit 122 and patient module 124 cooperate to send electrical stimulation signals to one or more of the stimulation electrodes provided on these Surgical Access Instruments. Depending upon the location within a patient (and more particularly, to any neural structures), the stimulation signals may cause nerves adjacent to or in the general proximity of the Surgical Access Instruments to depolarize. This causes muscle groups to innervate and generate EMG responses, which can be sensed via the EMG harness 126. The nerve direction feature of the system 120 is based on assessing the evoked response of the various muscle myotomes monitored by the system 120 via the EMG harness 126.

By monitoring the myotomes associated with the nerves (via the EMG harness 126 and recording electrode 127) and assessing the resulting EMG responses (via the control unit 122), the surgical access system of the present invention is capable of detecting the presence of (and optionally the distant and/or direction to) such nerves. This provides the ability to actively negotiate around or past such nerves to safely and reproducibly form the operative corridor to a particular surgical target site, as well as monitor to ensure that no neural structures migrate into contact with the retraction assembly 10 after the operative corridor has been established. In spinal surgery, for example, this is particularly advantageous in that the surgical access system of the present invention may be particularly suited for establishing an operative corridor to an intervertebral target site in a postero-lateral, trans-psoas fashion so as to avoid the bony posterior elements of the spinal column.

According to one embodiment, the surgical access system detects the presence of (and optionally, the distance and/or direction to) nerves by determining a stimulation current threshold level ("$I_{thresh}$") required to evoke a predetermined neuromuscular response (e.g. an EMG response of 100 uV). $I_{thresh}$ decreases as the degree of electrical communication between a stimulation impulse and a nerve increases. Thus, $I_{thresh}$ is indicative of the degree of communication between a stimulation source and a nerve and may therefore provide the user (by way of example only) with an indication of proximity to the nerve.

In order to quickly determine $I_{thresh}$, the system may employ a threshold-hunting algorithm. According to one embodiment, the threshold-hunting algorithm employs a series of monopolar stimulations to determine the stimulation current threshold for each EMG channel that is in scope. The nerve is stimulated using current pulses with amplitude of $I_{stim}$. The muscle groups respond with an evoked potential that has a peak to peak voltage of $V_{pp}$. $I_{thresh}$ is the minimum $I_{stim}$ that results in a $V_{pp}$ that is greater than a known threshold voltage $V_{thresh}$. The value of $I_{stim}$ is adjusted by a bracketing method as follows. The first bracket comprises two stimulation signals of different $I_{stim}$. By way of example the first bracket may comprise 0.2 mA and 0.3 mA. If the $V_{pp}$ corresponding to both of these stimulation currents is lower than $V_{thresh}$, then the bracket size is doubled to 0.2 mA and 0.4 mA. This exponential doubling of the bracket size continues until the upper end of the bracket results in a $V_{pp}$ that is above $V_{thresh}$. The size of the brackets is then reduced by a bisection method. A current stimulation value at the midpoint of the bracket is used and if this results in a $V_{pp}$ that is above $V_{thresh}$, then the lower half becomes the new bracket. Likewise, if the midpoint $V_{pp}$ is below $V_{thresh}$ then the upper half becomes the new bracket. This bisection method is used until the bracket size has been reduced to a predetermined accuracy. $I_{Thresh}$ may be selected from any value within the final bracket. By way of example, $I_{thresh}$ may be selected as the midpoint of the final bracket.

Figure 13:
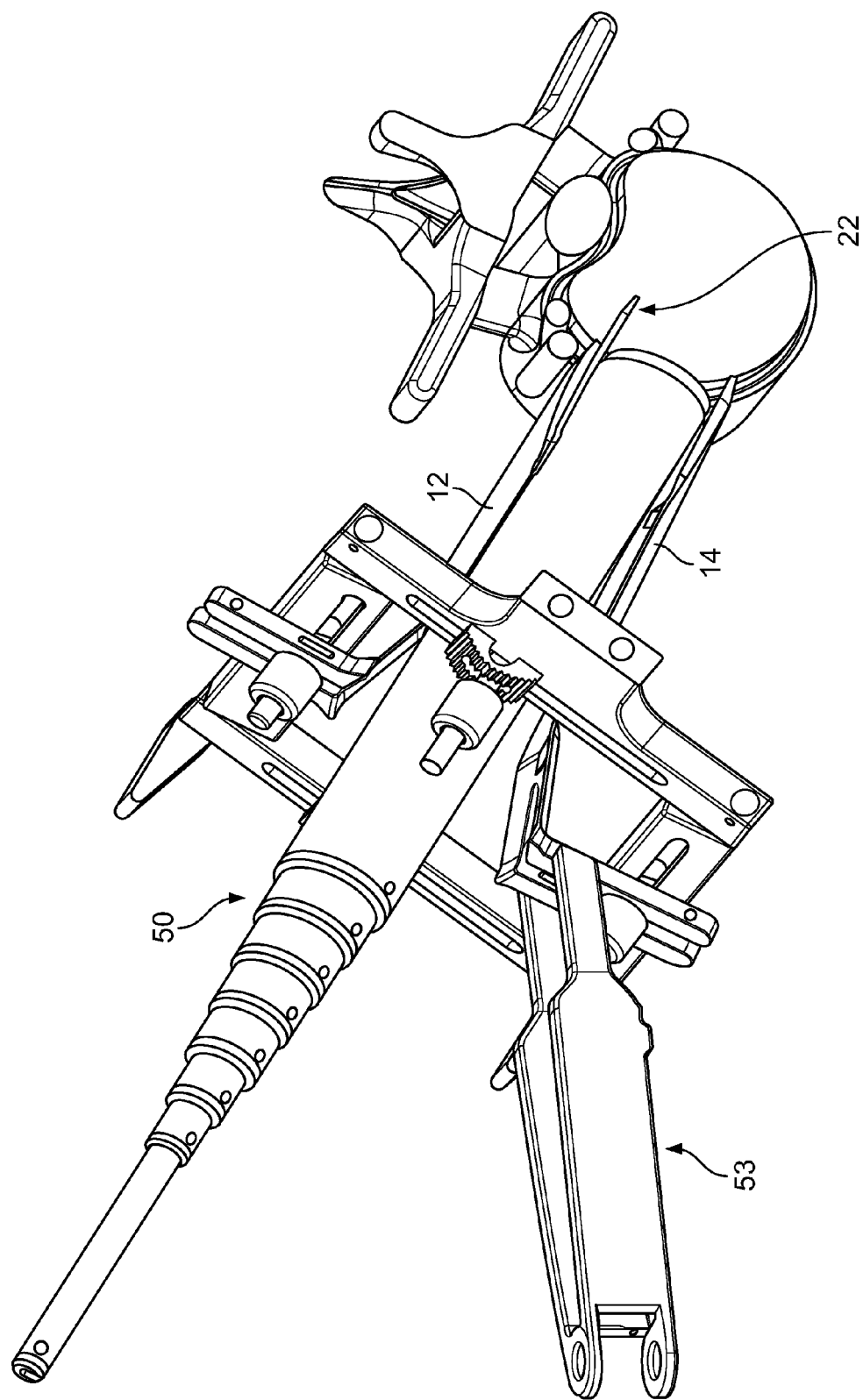
FIG. 13 is a perspective view of the anterior retractor blade 14 being moved away from the posterior retractor blade 12 through the use of a plurality of sequentially dilating cannula 50.
Figure 18:
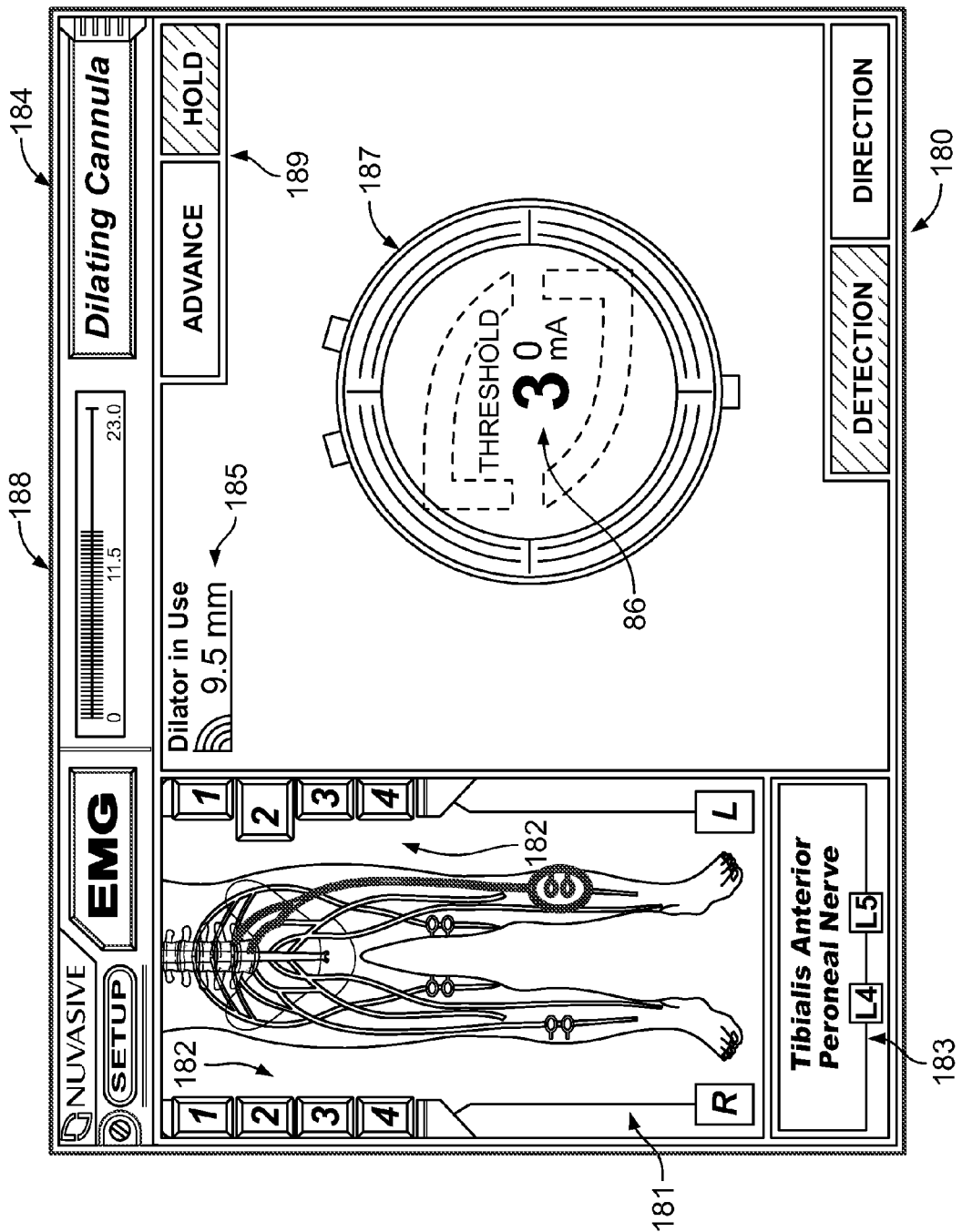
FIGS. 18-19 are screen displays illustrating exemplary features and information communicated to a user during the use of the nerve monitoring system of FIG. 16.
Figure 19:
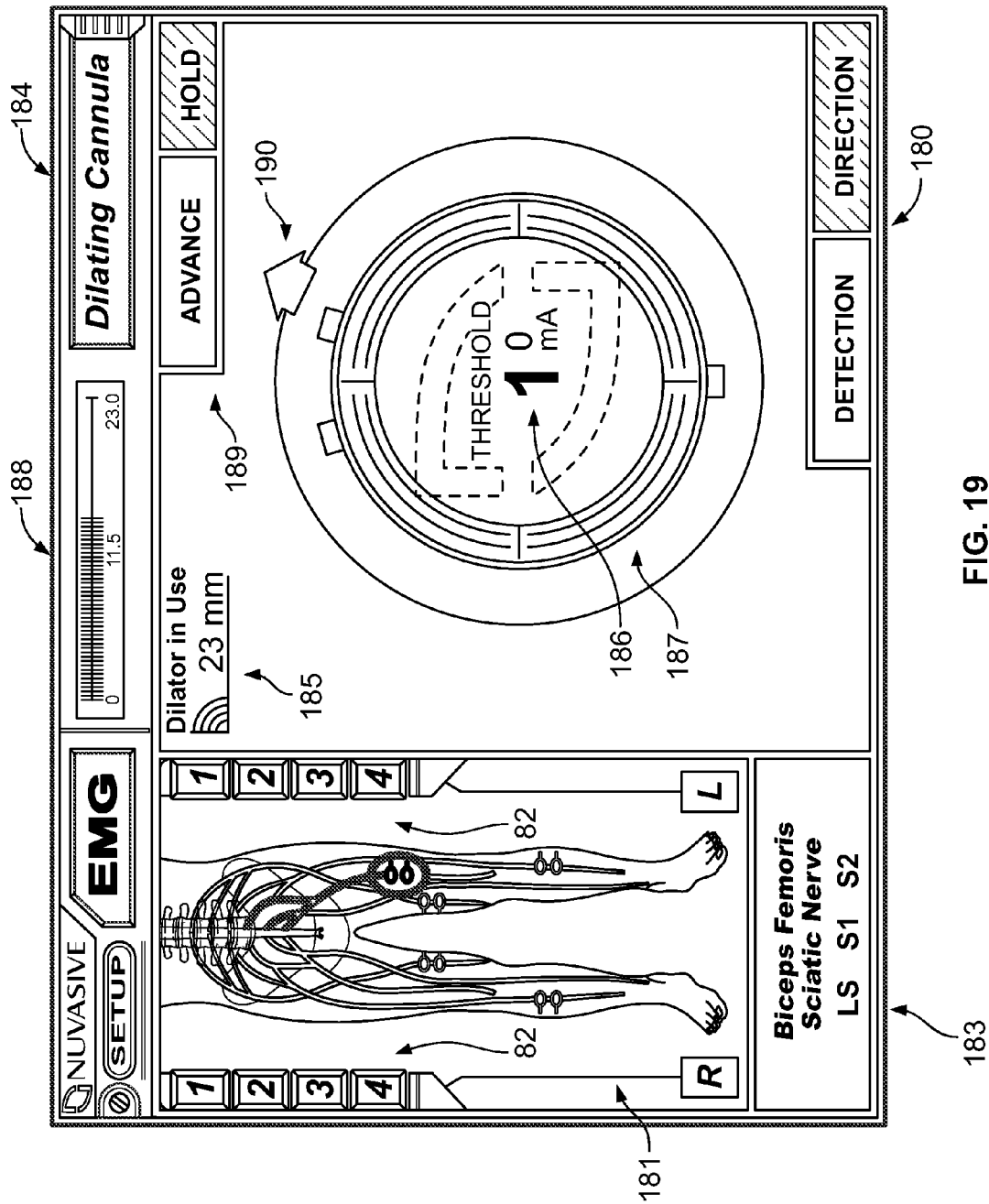

FIGS. 18-19 are exemplary screen displays (to be shown on the display 140) illustrating one embodiment of the nerve direction feature of the monitoring system shown and described with reference to FIGS. 16-17. These screen displays are intended to communicate a variety of information to the surgeon in an easy-to-interpret fashion. This information may include, but is not necessarily limited to, a display of the function 180 (in this case "DIRECTION"), a graphical representation of a patient 181, the myotome levels being monitored 182, the nerve or group associated with a displayed myotome 183, the name of the instrument being used 184 (e.g. dilating cannula 44), the size of the instrument being used 185, the stimulation threshold current 186, a graphical representation of the instrument being used 187 (in this case, a cross-sectional view of a dilating cannula 44) to provide a reference point from which to illustrate relative direction of the instrument to the nerve, the stimulation current being applied to the stimulation electrodes 188, instructions for the user 189 (in this case, "ADVANCE" and/or "HOLD"), and (in FIG. 19) an arrow 190 indicating the direction from the instrument to a nerve. This information may be communicated in any number of suitable fashions, including but not limited to the use of visual indicia (such as alpha-numeric characters, light-emitting elements, and/or graphics) and audio communications (such as a speaker element). Although shown with specific reference to a dilating cannula (such as at 184), it is to be readily appreciated that the present invention is deemed to include providing similar information on the display 140 during the use of any or all of the various Surgical Access Instruments of the present invention, including the initial distraction assembly 40 (i.e. the K-wire 42, dilating cannula 44, and split dilator 48), the secondary distraction assembly 50 (FIGS. 13-14), and/or the retractor blades 12-18 and/or shim elements 22, 24 of the retraction assembly 10.

The initial distraction assembly 40 (FIG. 7) may be provided with one or more electrodes for use in providing the neural monitoring capabilities of the present invention. By way of example only, the K-wire 42 may be equipped with a distal electrode 60. This may be accomplished by constructing the K-wire 42 for a conductive material, providing outer layer of insulation extending along the entire length with the exception of an exposure that defines the electrode 60. The electrode 60 has an angled configuration relative to the rest of the K-wire 42 (such as, by way of example only, in the range of between 15 and 75 degrees from the longitudinal axis of the K-wire 42). The angled nature of the electrode 60 is advantageous in that it aids in piercing tissue as the K-wire 42 is advanced towards the surgical target site.

The angled nature of the distal electrode 60 is also important in that it provides the ability to determine the location of nerves or neural structures relative to the K-wire 42 as it is advanced towards or resting at or near the surgical target site. This "directional" capability is achieved by the fact that the angled nature of the electrode 60 causes the electrical stimulation to be projected away from the distal portion of the K-wire 42 in a focused, or directed fashion. The end result is that nerves or neural structures which are generally closer to the side of the K-wire 42 on which the electrode 60 is disposed will have a higher likelihood of firing or being innervated that nerves or neural structures on the opposite side as the electrode 60.

The direction to such nerves or neural structures may thus be determined by physically rotating the K-wire 42 at a particular point within the patient's tissue and monitoring to see if any neural stimulation occurs at a given point within the rotation. Such monitoring can be performed via visual observation, a traditional EMG monitoring, as well as the nerve surveillance system disclosed in the above-referenced NeuroVision Applications. If the signals appear more profound or significant at a given point within the rotation, the surgeon will be able tell where the corresponding nerves or neural structures are, by way of example only, by looking at reference information (such as the indicia) on the exposed part of the K-wire 42 (which reference point is preferably set forth in the exact same orientation as the electrode 60).

The dilating cannula 44 and split dilator 48 may also be provided with electrodes (flat electrodes 64 and angled electrodes 62, respectively) for the purpose of determining the location of nerves or neural structures relative to the dilating cannula 44 and split-dilator 48 are advanced over the K-wire 44 towards or positioned at or near the surgical target site. Electrodes 62, 64 may be provided via any number of suitable methods, including but not limited to providing electrically conductive elements within the walls of the dilating cannula 44 and split dilator 48, such as by manufacturing them from plastic or similar material capable of injection molding or manufacturing them from aluminum (or similar metallic substance) and providing outer insulation layer with exposed regions (such as by anodizing the exterior of the aluminum dilator).

The secondary distraction assembly (including the sequential dilation assembly 50 of FIGS. 13-14) may be provided with one or more electrodes for use in providing the neural monitoring capabilities of the present invention. By way of example only, it may be advantageous to provide one or more electrodes on the dilating cannulae comprising the sequential dilation assembly 50 for the purpose of conducting neural monitoring before, during and/or after the secondary distraction.

The retractor blades 12-18 and the shim elements 22, 24 of the present invention may also be provided with one or more electrodes for use in providing the neural monitoring capabilities of the present invention. By way of example only, it may be advantageous to provide one or more electrodes on these components (preferably on the side facing away from the surgical target site) for the purpose of conducting neural monitoring before, during and/or after the retractor blades 12-18 and/or shim elements 22, 24 have been positioned at or near the surgical target site.

The surgical access system of the present invention may be sold or distributed to end users in any number of suitable kits or packages (sterile and/or non-sterile) containing some or all of the various components described herein. For example, the retraction assembly 10 may be provided such that the mounting assembly 20 is reusable (e.g., autoclavable), while the retractor blades 12-18 and/or shim elements 22, 24 are disposable. In a further embodiment, an initial kit may include these materials, including a variety of sets of retractor blades 12-18 and/or shim elements 22, 24 (and extensions 80) having varying (or "incremental") lengths to account for surgical target sites of varying locations within the patient, optionally color-coded to designate a predetermined length.

As evident from the above discussion and drawings, the present invention accomplishes the goal of providing a novel surgical access system and related methods which involve creating a distraction corridor to a surgical target site, thereafter retracting the distraction corridor to establish and maintain an operative corridor to the surgical target site, and optionally detecting the existence of (and optionally the distance and/or direction to) neural structures before, during and/or after the formation of the distraction and/or operative corridors.

The steps of distraction followed by retraction are advantageous because they provide the ability to more easily position an operative corridor-establishing device through tissue that is strong, thick or otherwise challenging to traverse in order to access a surgical target site. The various distraction systems of the present invention are advantageous in that they provide an improved manner of atraumatically establishing a distraction corridor prior to the use of the retraction systems of the present invention. The various retractor systems of the present invention are advantageous in that they provide an operative corridor having improved cross-sectional area and shape (including customization thereof) relative to the prior art surgical access systems. Moreover, by optionally equipping the various distraction systems and/or retraction systems with one or more electrodes, an operative corridor may be established through (or near) any of a variety of tissues having such neural structures which, if contacted or impinged, may otherwise result in neural impairment for the patient.

The surgical access system of the present invention can be used in any of a wide variety of surgical or medical applications, above and beyond the spinal applications discussed herein. By way of example only, in spinal applications, any number of implants and/or instruments may be introduced through the working cannula 50, including but not limited to spinal fusion constructs (such as allograft implants, ceramic implants, cages, mesh, etc.), fixation devices (such as pedicle and/or facet screws and related tension bands or rod systems), and any number of motion-preserving devices (including but not limited to nucleus replacement and/or total disc replacement systems).

While certain embodiments have been described, it will be appreciated by those skilled in the art that variations may be accomplished in view of these teachings without deviating from the spirit or scope of the present application. For example, with regard to the monitoring system 120, it may be implemented using any combination of computer programming software, firmware or hardware. As a preparatory act to practicing the system 120 or constructing an apparatus according to the application, the computer programming code (whether software or firmware) according to the application will typically be stored in one or more machine readable storage mediums such as fixed (hard) drives, diskettes, optical disks, magnetic tape, semiconductor memories such as ROMs, PROMs, etc., thereby making an article of manufacture in accordance with the application. The article of manufacture containing the computer programming code may be used by either executing the code directly from the storage device, by copying the code from the storage device into another storage device such as a hard disk, RAM, etc. or by transmitting the code on a network for remote execution. As can be envisioned by one of skill in the art, many different combinations of the above may be used and accordingly the present application is not limited by the scope of the appended claims.

What is claimed is:

1. A method of accessing a spinal target site via a lateral, trans-psoas surgical approach, comprising the steps of:
    establishing a distraction corridor via a lateral, trans-psoas surgical approach to said spinal target site with a distraction assembly prior to the introduction of a first retractor blade;
    affixing said first retractor blade introduced to said spinal target site via said lateral, trans-psoas approach such that said first retractor blade forms a posterior border of an operative corridor along said lateral, trans-psoas surgical approach to said spinal target site and is fixed relative to said spinal target site, wherein affixing said first retractor blade is accomplished with a fixation element removably engaged with said first retractor blade after said first retractor blade is introduced to said spinal target site and such that a distal tip of said fixation element extends past said first retractor blade and penetrates into the spinal target site; and
    moving a second retractor blade introduced to said spinal target site via said lateral, trans-psoas approach relative to said affixed first retractor blade such that said operative corridor is established between said first and second retractor blades to said spinal target site.

2. The method of claim 1, wherein said first retractor blade is introduced to said spinal target site before said second retractor blade is introduced to said spinal target site.

3. The method of claim 1, wherein said step of moving said second retractor blade relative to said affixed first retractor blade is accomplished by using a distraction system.

4. The method of claim 3, wherein said distraction system comprises a sequential dilation system disposed in between said first and second retractor blades to sequentially move said first and second retractor blades apart from one another.

5. The method of claim 1, wherein said distraction assembly includes a plurality of dilators and a K-wire, wherein said plurality of dilators are capable of being passed over said K-wire.

6. The method of claim 5, wherein said plurality of dilators of said distraction assembly includes a dilating cannula and at least two dilator members disposed within said dilating cannula, wherein said at least two dilator members and said dilating cannula are capable of being slideably passed over said K-wire.

7. The method of claim 1, further comprising the step of performing neuromonitoring during at least one of establishing said distraction corridor and establishing said operative corridor to the spinal target site.

8. The method of claim 7, wherein said step of performing neuromonitoring comprises activating a control unit that: stimulates a stimulation electrode on at least one of the distraction assembly and said first retractor blade, senses a response of a nerve depolarized by said stimulation, determines at least one of nerve proximity and nerve direction based on said sensed response, and communicates said at least one of nerve proximity and nerve direction to a surgeon performing said surgery.

9. The method of claim 8, wherein said sensing of said depolarized nerve is accomplished through the use of a recording electrode configured to sense a neuromuscular response of a muscle coupled to said depolarized nerve, the recording electrode being communicatively linked to the control unit.

10. The method of claim 8, wherein said communication of said at least one of nerve proximity and nerve direction is accomplished through the use of a display communicatively linked to said control unit and operable to display an electromyographic (EMG) response of a muscle coupled to said nerve depolarized by said stimulation.

11. The method of claim 10, wherein said display comprises a touch-screen display operable to receive commands from a user.

12. The method of claim 8, wherein said stimulation electrode is positioned on a posteriorly facing surface of said first retractor blade and said electrode is stimulated as first retractor blade is introduced to said spinal target site.

13. The method of claim 8, wherein said step of determining at least one of nerve proximity and nerve direction includes determining a threshold stimulation level required to evoke said neuromuscular response and wherein said step of determining a threshold stimulation level includes establishing first a bracket containing said threshold stimulation level and bisecting said bracket to form a smaller second bracket containing said threshold stimulation level.

14. The method of claim 1, wherein said step of affixing the fixation element is a shim element that removably engages with an inward facing surface of said first retractor blade such that a distal tip of said shim element extends past said first retractor blade and penetrates into a lumbar intevertebral disc comprising the spinal target site.

15. The method of claim 14, wherein said shim element engages a groove formed in the inward facing surface of said first retractor blade after said first retractor blade is introduced to said surgical target site.

16. The method of claim 1, wherein said second retractor blade is affixed to said spinal target site after being moved relative to said first retractor blade.

17. A method of accessing a spinal target site via a lateral, trans-psoas surgical approach, comprising the steps of:
introducing a first retractor blade and a second retractor blade to said spinal target site via a lateral, trans-psoas surgical approach such that said first retractor blade is positioned along a posterior aspect of a lumbar intervertebral disc comprising said spinal target site and comprises a posterior border of an operative corridor along said lateral, trans-psoas surgical approach to said spinal target site;
penetrating the intervertebral disc with a shim element removeably engaged to said first retractor blade after introducing said first retractor blade to said spinal target site and extending from a distal end of the first retractor blade so as to affix said first retractor blade relative to said spinal target site;
moving said second retractor blade relative to said affixed first retractor blade to establish said operative corridor along said lateral, trans-psoas surgical approach between said first and second retractor blades to said spinal target site; and
passing an implant toward said spinal target site through said operative corridor established between said first retractor blade and said second retractor blade.

18. The method of claim 17, wherein said first retractor blade is introduced to said spinal target site before said second retractor blade is introduced to said spinal target site.

19. The method of claim 17, wherein said step of moving said second retractor blade relative to said affixed first retractor blade is accomplished by using a distraction system.

20. The method of claim 19, wherein said distraction system comprises a sequential dilation system disposed in between said first and second retractor blades to sequentially move said first and second retractor blades apart from one another.

21. The method of claim 17, further comprising the step of establishing an initial distraction corridor through the use of an initial distraction assembly via said lateral, trans-psoas surgical approach to said spinal target site prior to the introduction of said first retractor blade.

22. The method of claim 21, further comprising the step of performing neuromonitoring during at least one of establishing said distraction corridor and establishing said operative corridor to the spinal target site.

23. The method of claim 22, wherein said step of performing neuromonitoring comprises activating a control unit that: stimulates a stimulation electrode on said first retractor blade, senses a response of a nerve depolarized by said stimulation, determines at least one of nerve proximity and nerve direction based on said sensed response, and communicates said at least one of nerve proximity and nerve direction to a surgeon performing said surgery.

24. The method of claim 23, wherein said stimulation electrode is positioned on a posteriorly facing surface of said first retractor blade and said electrode is stimulated as first retractor blade is introduced to said spinal target site.

25. The method of claim 22, wherein said step of performing neuromonitoring comprises activating a control unit that: stimulates a stimulation electrode on the distraction assembly, senses a response of a nerve depolarized by said stimulation, determines at least one of nerve proximity and nerve direction based on said sensed response, and communicates said at least one of nerve proximity and nerve direction to a surgeon performing said surgery.

26. The method of claim 25, wherein said sensing of said depolarized nerve is accomplished through the use of a recording electrode configured to sense a neuromuscular response of a muscle coupled to said depolarized nerve, the recording electrode being communicatively linked to the control unit.

27. The method of claim 25, wherein said communication of said at least one of nerve proximity and nerve direction is accomplished through the use of a display communicatively linked to said control unit and operable to display an electromyographic (EMG) response of a muscle coupled to said nerve depolarized by said stimulation.

28. The method of claim 27, wherein said display comprises a touch-screen display operable to receive commands from a user.

29. The method of claim 25, wherein said step of determining at least one of nerve proximity and nerve direction includes determining a threshold stimulation level required to evoke said neuromuscular response and wherein said step of determining a threshold stimulation level includes establishing first a bracket containing said threshold stimulation level and bisecting said bracket to form a smaller second bracket containing said threshold stimulation level.

30. The method of claim 21, wherein said initial distraction assembly includes: a plurality of dilators having one or more stimulation electrodes, and a K-wire, wherein said plurality of dilators are capable of being passed over said K-wire.

31. The method of claim 17, wherein said shim element slidably engages with a groove formed in a surface of said first retractor blade facing toward said operative corridor after said first blade is introduced to said spinal target site.

32. The method of claim 17, wherein after said second retractor blade is moved relative to said first retractor blade, said second retractor blade is affixed to said spinal target site.

33. A method of accessing a targeted site on the spine of a patient via a lateral, trans-psoas surgical approach, comprising the steps of:
establishing an initial distraction corridor through the use of an initial distraction assembly via a lateral, trans-psoas surgical approach to a targeted site on said spine while performing neuromonitoring during insertion of said initial distraction assembly via said lateral, trans-psoas surgical approach to the targeted site, wherein at least a component of the initial distraction assembly penetrates into an intervertebral disc of said spine;
after establishing said initial distraction corridor, introducing a first retractor blade to said targeted site on said spine via a lateral, trans-psoas surgical approach such that said first retractor blade is positioned in a first position along said spine;
after said first retractor blade is positioned in said first position along said spine, removably engaging an extension element to said first retractor blade such that the extension element extends from said first retractor blade into said spine to affix said first retractor blade relative to said spine;
moving a second retractor blade away from said affixed first retractor blade such that an operative corridor is established between said first and second retractor blades to said targeted site on said spine.

34. The method of claim 33, wherein said first retractor blade is introduced to said spinal target site before said second retractor blade is introduced to said spinal target site.

35. The method of claim 33, wherein said step of moving said second retractor blade relative to said affixed first retractor blade is accomplished by using a distraction system.

36. The method of claim 35, wherein said distraction system comprises a sequential dilation system disposed in between said first and second retractor blades to sequentially move said first and second retractor blades apart from one another.

37. The method of claim 33, wherein said initial distraction assembly includes: a plurality of dilators having one or more stimulation electrodes, and a K-wire, wherein said plurality of dilators are capable of being passed over said K-wire.

38. The method of claim 33, wherein said first extension element comprises a shim member slidably engaged to said first retractor blade and said second extension element comprises a shim member slidably engaged to said second retractor blade.

39. The method of claim 33, wherein said step of performing neuromonitoring during insertion of said initial distraction assembly includes activating a control system that: stimulates at least one stimulation electrode on said initial distraction assembly, senses a response of a nerve depolarized by said stimulation, determines at least one of nerve proximity and nerve direction based on said sensed response, and communicates said at least one nerve proximity and nerve direction to a surgeon performing said surgery.

40. The method of claim 39, wherein said communication of said at least one of nerve proximity and nerve direction is accomplished through the use of a display communicatively linked to said control unit and operable to display an electromyographic (EMG) response of a muscle coupled to said nerve depolarized by said stimulation.

41. The method of claim 40, wherein said display comprises a touch-screen display operable to receive commands from a user.

42. The method of claim 33, further comprising performing neuromonitoring during introduction of said first retractor blade by using a neuromonitoring system including a control unit capable of stimulating at least one stimulation electrode arranged on said first retractor blade, sensing a response of a nerve depolarized by said stimulation, determining at least one of nerve proximity and nerve direction based on said sensed response, and communicating said at least one nerve proximity and nerve direction to a surgeon performing said surgery.

43. The method of claim 42, wherein said sensing of said depolarized nerve is accomplished through the use of a recording electrode configured to sense a neuromuscular response of a muscle coupled to said depolarized nerve, the recording electrode being communicatively linked to the control unit.

44. The method of claim 42, wherein said at least one stimulation electrode is positioned on a posteriorly facing surface of said first retractor blade.

45. The method of claim 42, wherein said step of determining at least one of nerve proximity and nerve direction includes determining a threshold stimulation level required to evoke said neuromuscular response and wherein said step of determining a threshold stimulation level includes establishing first a bracket containing said threshold stimulation level and bisecting said bracket to form a smaller second bracket containing said threshold stimulation level.

46. The method of claim 42, wherein said first position along said spine is a posterior region of an intervertebral disc of said spine.

47. The method of claim 46, wherein said second position along said spine is an anterior region of said intervertebral disc of said spine.

48. The method of claim 33, wherein said second retractor blade is positioned angularly relative to said first retractor blade before being affixed to said spinal target site.

* * * * *